United States Patent
Baek et al.

(10) Patent No.: US 11,844,591 B2
(45) Date of Patent: Dec. 19, 2023

(54) MULTI-MODEL BLOOD PRESSURE ESTIMATION

(71) Applicant: QUALCOMM Incorporated, San Diego, CA (US)

(72) Inventors: David Boettcher Baek, San Diego, CA (US); Lars Lading, Roskilde (DK)

(73) Assignee: QUALCOMM Incorporated, San Diego, CA (US)

( * ) Notice: Subject to any disclaimer, the term of this patent is extended or adjusted under 35 U.S.C. 154(b) by 805 days.

(21) Appl. No.: 15/268,292

(22) Filed: Sep. 16, 2016

(65) Prior Publication Data
US 2018/0078155 A1 Mar. 22, 2018

(51) Int. Cl.
| | |
|---|---|
| A61B 5/021 | (2006.01) |
| G16H 50/50 | (2018.01) |
| A61B 5/026 | (2006.01) |
| A61B 5/0285 | (2006.01) |
| G16H 40/40 | (2018.01) |

(Continued)

(52) U.S. Cl.
CPC ........ *A61B 5/02125* (2013.01); *A61B 5/0059* (2013.01); *A61B 5/026* (2013.01); *A61B 5/02007* (2013.01); *A61B 5/0261* (2013.01); *A61B 5/0285* (2013.01); *A61B 5/0295* (2013.01); *A61B 5/7278* (2013.01); *A61B 5/742* (2013.01); *A61B 8/04* (2013.01);

(Continued)

(58) Field of Classification Search
CPC ............ A61B 5/021; A61B 2560/0261; A61B 2560/0223
See application file for complete search history.

(56) References Cited

U.S. PATENT DOCUMENTS

| | | |
|---|---|---|
| 5,241,964 A | 9/1993 | McQuilkin |
| 7,425,199 B2 | 9/2008 | Hoctor et al. |

(Continued)

FOREIGN PATENT DOCUMENTS

CN 104706348 A 6/2015

OTHER PUBLICATIONS

International Search Report and Written Opinion—PCT/US2017/047214—ISA/EPO—dated Nov. 13, 2017.

*Primary Examiner* — Tse W Chen
*Assistant Examiner* — Michael A Catina
(74) *Attorney, Agent, or Firm* — QUALCOMM Incorporated

(57) ABSTRACT

One aspect of the subject matter described in this disclosure can be implemented in a device capable of use in estimating blood pressure. The device includes one or more arterial sensors configured to obtain arterial measurements at two or more elevations. The device additionally includes one or more processors configured to determine one or more calibration parameters for a first blood pressure model based on the arterial measurements and a hydrostatic pressure difference between at least two of the elevations. The processors also are configured to determine a first blood pressure based on the first blood pressure model, the calibration parameters and the arterial measurements. The processors also are configured to determine a second blood pressure based in part on a second blood pressure model, one or more calibration parameters and the arterial measurements. The processors are further configured to provide a final blood pressure based on the first and second blood pressures.

23 Claims, 16 Drawing Sheets

(51) Int. Cl.
  *G16H 50/30* (2018.01)
  *A61B 5/0295* (2006.01)
  *A61B 5/00* (2006.01)
  *A61B 5/02* (2006.01)
  *A61B 8/04* (2006.01)

(52) U.S. Cl.
  CPC ............ *G16H 40/40* (2018.01); *G16H 50/30* (2018.01); *G16H 50/50* (2018.01); *A61B 2560/0223* (2013.01)

(56) References Cited

U.S. PATENT DOCUMENTS

| | | |
|---|---|---|
| 7,674,231 B2 | 3/2010 | McCombie et al. |
| 8,162,841 B2 | 4/2012 | Keel et al. |
| 8,672,854 B2 | 3/2014 | McCombie et al. |
| 2008/0039731 A1* | 2/2008 | McCombie ........ A61B 5/02125 600/485 |
| 2008/0306354 A1* | 12/2008 | Mason .................. G16H 40/63 600/301 |
| 2009/0281434 A1* | 11/2009 | Messerges ........... G09B 23/288 600/485 |
| 2010/0049059 A1* | 2/2010 | Ha ..................... A61B 5/02125 600/509 |
| 2011/0066010 A1 | 3/2011 | Moon et al. |
| 2015/0327784 A1 | 11/2015 | Lading et al. |
| 2015/0327785 A1 | 11/2015 | Lading et al. |

* cited by examiner

MULTI-MODEL BLOOD PRESSURE ESTIMATION

TECHNICAL FIELD

This disclosure relates generally to sensing devices, and more particularly, to blood pressure estimation devices capable of use in sensing arterial data and determining a patient's blood pressure based on the arterial data using at least two different models.

DESCRIPTION OF RELATED TECHNOLOGY

A variety of different sensing technologies and algorithms are being investigated for use in various biomedical applications, including health and wellness monitoring. This push is partly a result of the limitations in the usability of traditional measuring devices for continuous, noninvasive and ambulatory monitoring. For example, a sphygmomanometer is an example of a traditional blood pressure estimation device that utilizes an inflatable cuff to apply a counter pressure to a region of interest (for example, around an upper arm of a subject). The pressure exerted by the inflatable cuff is designed to restrict arterial flow in order to provide a measurement of systolic and diastolic pressure. Such traditional sphygmomanometers inherently affect the physiological state of the subject, which can introduce an error in the blood pressure measurements. Such sphygmomanometers also can affect the psychological state of the subject, which can manifest itself in a physiological state change, and thus, introduce an error in the blood pressure measurements. For example, such devices are often used primarily on isolated occasions, for example, when a subject visits a doctor's office or is being treated in a hospital setting. Naturally, some subjects experience anxiety during such occasions, and this anxiety can influence (for example, increase) the user's blood pressure as well as heart rate.

Additionally, such traditional sphygmomanometers are not portable in the sense that they cannot be worn without restriction of ambulatory movement, or are otherwise inhibiting, interfering or distracting. For these and other reasons, such devices do not provide an accurate estimation or "picture" of blood pressure, and a user's health in general, over time. While implanted or otherwise invasive devices may provide better estimates of blood pressure over time, such invasive devices generally involve greater risk than noninvasive devices and are generally not suitable for ambulatory use.

SUMMARY

The systems, methods and devices of this disclosure each have several aspects, no single one of which is solely responsible for the desirable attributes disclosed herein.

One aspect of the subject matter described in this disclosure can be implemented in a method capable of use in estimating blood pressure. In some implementations, the method includes obtaining arterial measurements of an artery at two or more elevations. The method also includes determining one or more calibration parameters for a first blood pressure model based on the arterial measurements and a hydrostatic pressure difference between at least two of the two or more elevations. The method also includes determining a first blood pressure in the artery based on the first blood pressure model, the one or more calibration parameters and the arterial measurements. The method also includes determining a second blood pressure in the artery based in part on a second blood pressure model, one or more calibration parameters and the arterial measurements. The method further includes providing a final blood pressure based on the first and the second blood pressures.

In some implementations, the method further includes comparing the first and the second blood pressures, and updating the one or more calibration parameters responsive to the comparison.

In some implementations, the arterial measurements include arterial distension measurements and arterial cross-sectional area measurements at each of the at least two elevations. In some such implementations, the determination of the one or more calibration parameters includes determining a mean arterial cross-sectional area for each of the at least two elevations, determining a mean arterial distension for each of the at least two elevations, and determining a first calibration parameter based on the mean arterial cross-sectional areas, the mean arterial distensions, and an arterial stress-strain relationship. In some implementations, the determination of the one or more calibration parameters includes determining a second calibration parameter based on the hydrostatic pressure difference and the first calibration parameter. In some implementations, the determination of the first blood pressure in the artery based on the first blood pressure model includes determining the first blood pressure using the stress-strain relationship.

In some implementations, the arterial measurements further include blood velocity measurements at each of the at least two elevations. In some such implementations, the method further includes determining blood flow measurements based on the arterial cross-sectional area measurements and the blood velocity measurements. In some such implementations, the determination of the one or more calibration parameters includes determining a calibration parameter based on the hydrostatic pressure difference and the arterial blood flow measurements based on a linear relationship between blood pressure and blood flow. In some such implementations, the determination of the first blood pressure in the artery based on the first blood pressure model includes determining the first blood pressure based on the linear relationship and the blood flow measurements.

In some implementations, the method further includes calibrating the second blood pressure model based on the first blood pressure. In some such implementations, the calibration of the second blood pressure model based on the first blood pressure includes solving a set of equations using the first blood pressure as an input to the set of equations. In some implementations, the determination of the second blood pressure in the artery based on the second blood pressure model includes determining a pulse wave velocity (PWV) based on the arterial measurements. In some such implementations, the determination of the PWV based on the arterial measurements includes determining a pulse transit time (PTT) between two arterial locations based on the arterial measurements, and determining the PWV based on the PTT and a distance between the two locations. In some other implementations in which the arterial measurements include arterial cross-sectional area measurements and arterial blood velocity measurements, the method further includes determining arterial blood flow measurements based on the arterial cross-sectional area measurements and the arterial blood velocity measurements. In some such implementations, the determination of the PWV based on the arterial measurements includes determining a derivative of the arterial blood flow measurements with respect to the arterial cross-sectional area measurements, and determining the PWV based on the derivative.

Another aspect of the subject matter described in this disclosure can be implemented in a device capable of use in estimating blood pressure. In some implementations, device includes one or more arterial sensors configured to obtain arterial measurements of an artery at two or more elevations. The device also includes one or more processors configured to determine one or more calibration parameters for a first blood pressure model based on the arterial measurements and a hydrostatic pressure difference between at least two of the two or more elevations. The one or more processors also are configured to determine a first blood pressure in the artery based on the first blood pressure model, the one or more calibration parameters and the arterial measurements. The one or more processors also are configured to determine a second blood pressure in the artery based in part on a second blood pressure model, one or more calibration parameters and the arterial measurements. The one or more processors are further configured to provide a final blood pressure based on the first and the second blood pressures.

In some implementations, the one or more processors are further configured to compare the first and the second blood pressures and update the one or more calibration parameters responsive to the comparison.

In some implementations, the arterial measurements include arterial distension measurements and arterial cross-sectional area measurements at each of the at least two elevations. In some such implementations, the determination of the one or more calibration parameters includes determining a mean arterial cross-sectional area for each of the at least two elevations, determining a mean arterial distension for each of the at least two elevations, and determining a first calibration parameter based on the mean arterial cross-sectional areas, the mean arterial distensions, and an arterial stress-strain relationship. In some implementations, the determination of the one or more calibration parameters includes determining a second calibration parameter based on the hydrostatic pressure difference and the first calibration parameter.

In some implementations, the arterial measurements further include blood velocity measurements at each of the at least two elevations, and the one or more processors are further configured to determine blood flow measurements based on the arterial cross-sectional area measurements and the blood velocity measurements. In some such implementations, the determination of the one or more calibration parameters includes determining a calibration parameter based on the hydrostatic pressure difference and the arterial blood flow measurements based on a linear relationship between blood pressure and blood flow.

In some implementations, the one or more processors are further configured to calibrate the second blood pressure model based on the first blood pressure. In some such implementations, the calibration of the second blood pressure model based on the first blood pressure includes solving a set of equations using the first blood pressure as an input to the set of equations. In some implementations, the determination of the second blood pressure in the artery based on the second blood pressure model includes determining a pulse wave velocity (PWV) based on the arterial measurements. In some such implementations, the determination of the PWV based on the arterial measurements includes determining a pulse transit time (PTT) between two arterial locations based on the arterial measurements, and determining the PWV based on the PTT and a distance between the two locations. In some other implementations in which the arterial measurements include arterial cross-sectional area measurements and arterial blood velocity measurements, the one or more processors are further configured to determine arterial blood flow measurements based on the arterial cross-sectional area measurements and the arterial blood velocity measurements. In some such implementations, the determining of the PWV based on the arterial measurements includes determining a derivative of the arterial blood flow measurements with respect to the arterial cross-sectional area measurements, and determining the PWV based on the derivative.

Another aspect of the subject matter described in this disclosure can be implemented in a device capable of use in estimating blood pressure. In some implementations, device includes means for obtaining arterial measurements of an artery at two or more elevations. The device also includes means for determining one or more calibration parameters for a first blood pressure model based on the arterial measurements and a hydrostatic pressure difference between at least two of the two or more elevations. The device also includes means for determining a first blood pressure in the artery based on the first blood pressure model, the one or more calibration parameters and the arterial measurements. The device also includes means for determining a second blood pressure in the artery based in part on a second blood pressure model, one or more calibration parameters and the arterial measurements. The device further includes means for providing a final blood pressure based on the first and the second blood pressures. In some implementations, the device additionally includes means for comparing the first and the second blood pressures, and means for updating the one or more calibration parameters responsive to the comparison.

Another aspect of the subject matter described in this disclosure can be implemented in one or more tangible computer-readable media storing non-transitory instructions executable by one or more processors to cause operations to be performed including obtaining arterial measurements of an artery at two or more elevations. The operations also include determining one or more calibration parameters for a first blood pressure model based on the arterial measurements and a hydrostatic pressure difference between at least two of the two or more elevations. The operations also include determining a first blood pressure in the artery based on the first blood pressure model, the one or more calibration parameters and the arterial measurements. The operations additionally include determining a second blood pressure in the artery based in part on a second blood pressure model, one or more calibration parameters and the arterial measurements. The operations further include providing a final blood pressure based on the first and the second blood pressures. In some implementations, the operations additionally include comparing the first and the second blood pressures, and updating the one or more calibration parameters responsive to the comparison.

Details of one or more implementations of the subject matter described in this disclosure are set forth in the accompanying drawings and the description below. Other features, aspects, and advantages will become apparent from the description, the drawings and the claims. Note that the relative dimensions of the following figures may not be drawn to scale.

BRIEF DESCRIPTION OF THE DRAWINGS

Like reference numbers and designations in the various drawings indicate like elements.

DETAILED DESCRIPTION

Figure 1:
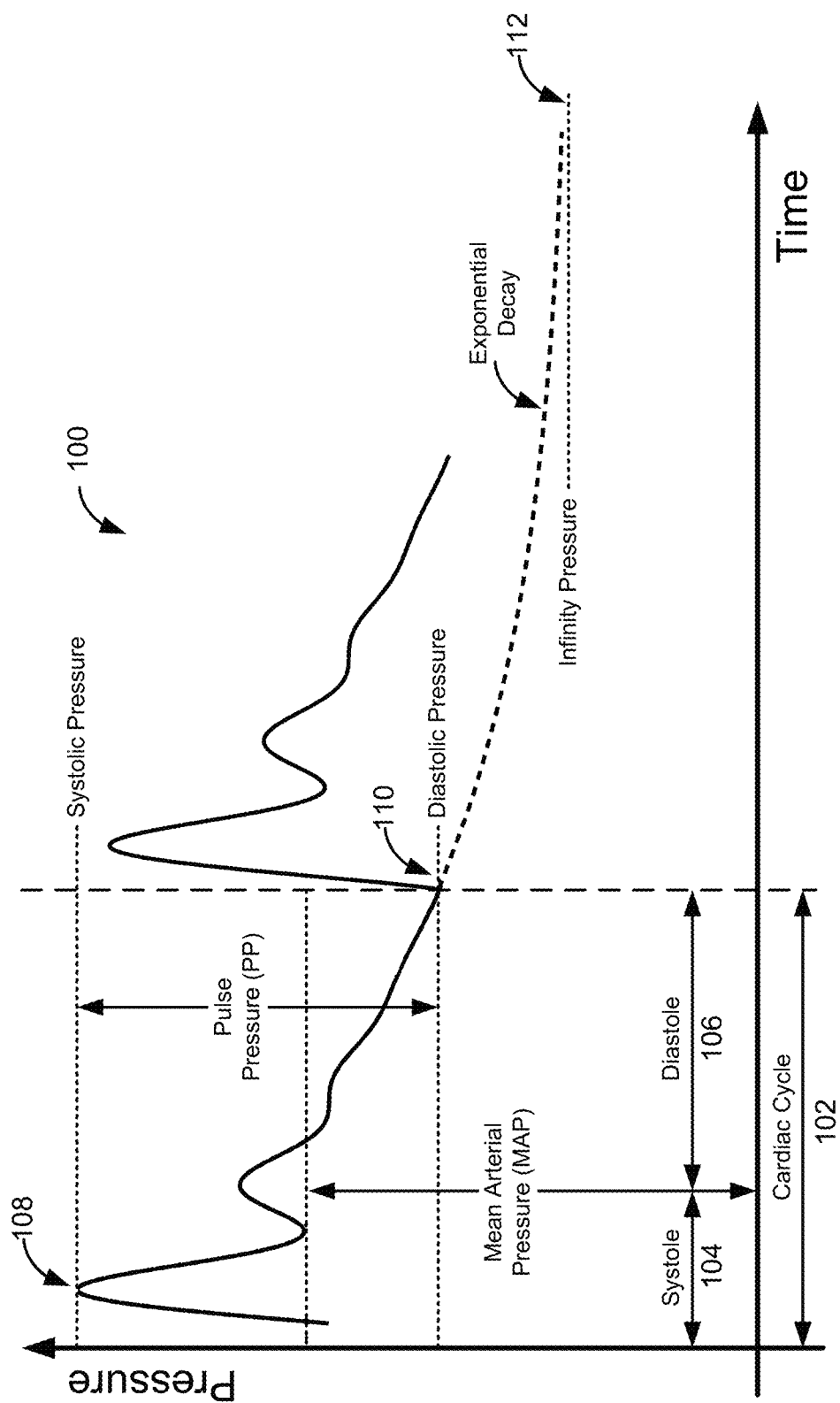
FIG. 1 shows a plot of an example blood pressure signal in an artery versus time during an example cardiac cycle.

The following description is directed to certain implementations for the purposes of describing various aspects of this disclosure. However, a person having ordinary skill in the art will readily recognize that the teachings herein can be applied in a multitude of different ways. Some of the concepts and examples provided in this disclosure are especially applicable to blood pressure estimation applications. However, some implementations also may be applicable to other types of biological sensing applications, as well as to other fluid flow systems. Thus, the teachings are not intended to be limited to the specific implementations depicted and described with reference to the drawings; rather, the teachings have wide applicability as will be apparent to persons having ordinary skill in the art.

This disclosure relates generally to devices, systems and methods for estimating various characteristics of interest (also referred to herein as "properties" or "signals") in a fluid flow system, and in particular, a pulsating fluid flow system. Various implementations are more particularly directed or applicable to devices, systems and methods for estimating various biological characteristics including, for example, dynamic or time-varying cardiovascular characteristics such as blood pressure, based at least in part on measurements of arterial data. Some implementations more specifically relate to a blood pressure estimation device for estimating a subject's transmural blood pressure based on at least two models. In some implementations, the at least two models include at least one model capable of self-calibration and at least one model capable of maintaining calibration after an initial pre-calibration. In some implementations, while capable of self-calibration, the first model can require movement or particular activity (such as a change in elevation of the blood pressure estimation device) to perform the self-calibration. In some implementations, the second model can be a non-self-calibrating blood pressure model. In some such implementations, while not capable of self-calibration, the second model can be a model that performs well at maintaining its calibration even in the absence of movement or activity (for example, while the user is sleeping).

In some implementations, during a calibration (or recalibration) operation, the self-calibrating model can be used to determine one or more calibration parameters needed for calibration based on, for example, changes in elevation associated with user movement or activity. The one or more calibration parameters can then be used in conjunction with the self-calibrating blood pressure model to determine a first value of the blood pressure. In some implementations, the first blood pressure value is then used to calibrate the second model.

In some implementations, during regular operation (after calibration), a blood pressure estimation device as disclosed herein can continuously or semi-continuously (for example, periodically) perform arterial measurements and compute a first blood pressure value based on the first self-calibrating blood pressure model, and in parallel, compute a second blood pressure value based on the second non-self-calibrating model. In some implementations, the blood pressure estimation device can then compare the first and the second blood pressure values. In some such implementations, the blood pressure estimation device can select a more reliable one of the first and the second blood pressure values to output or store. In some other implementations, the blood pressure estimation device can average or otherwise manipulate or combine the first and the second blood pressure values into a third ("final") blood pressure value to output or store. In some implementations, the blood pressure estimation device can perform a re-initialization or other re-calibration operation in which the first and the second models are re-calibrated in response to a determination that a sequence of one or more first blood pressure values (a "first blood pressure signal") and a sequence of one or more second blood pressure values (a "second blood pressure signal") have diverged. Such divergence can indicate that one or more of the calibration parameters have changed, for example, as a result of the arterial walls dilating or contracting or otherwise becoming more elastic (less stiff) or less elastic (more stiff).

Some implementations further relate to calibration and validation techniques, and more specifically, to calibration techniques based on hydrostatic pressure measurements. In particular, such calibration techniques do not require external reference devices or the use of known or inferred person-specific attributes. In some implementations, the calibration techniques provide full initial calibration as well as continued or regular updating of calibration based on user activity. Such initial and subsequent updating of calibration enables accurate blood pressure estimation, as well as the accurate estimation and monitoring of other cardiovascular system characteristics, even as cardiovascular properties change over time, for example, as the arterial walls dilate or contract or otherwise become more elastic or less elastic.

Particular implementations of the subject matter described in this disclosure can be implemented to realize one or more of the following potential advantages. Some implementations provide a robust and reliable way to estimate a subject's blood pressure in substantially real time regardless of the state of the subject or the activity the subject is engaged in. Some implementations provide initial calibration and continued updating or validation of calibration without the use of an external reference device or any externally applied counter pressure. Some implementations of the blood pressure estimation devices described herein also are designed to consume relatively little power enabling continuous wearing, estimation and monitoring of a biological signal of interest, such as an arterial distension waveform or a blood pressure, over extended durations of time (for example, hours, days, weeks or even a month or more) without external calibration, recharging or other interruption. Continuous monitoring generally provides greater prognostic and diagnostic value than isolated measurements, for example, obtained in a hospital or doctor's office setting.

Some implementations of the blood pressure estimation devices described herein also are designed with small form factors and with housings that can be coupled to a subject (also referred to herein as a "patient," "person" or "user") so as to be wearable, noninvasive, and nonrestrictive of ambulatory use. In other words, some implementations of the ambulatory monitoring devices described herein do not restrict the free uninhibited motion of a subject's arms or legs enabling continuous or periodic monitoring of cardiovascular characteristics such as blood pressure even as the subject is mobile or otherwise engaged in a physical activity. Not only do such devices not interfere with the subject's daily or other desired activities, they also may encourage continuous wearing by virtue of such non-interference. In some implementations, it can further be desirable that the subject has no notion about when the sensing device(s) of the blood pressure estimation device is actually performing measurements.

As used herein, the term "pulse pressure" refers to the difference between the systolic pressure and the diastolic pressure for a given cardiac cycle. Pulse pressure is generally not affected by local changes in the hydrostatic pressure in an artery in the peripheral regions of the body of a subject. As used herein, the term "transmural pressure" refers to the pressure difference between the pressure inside a particular artery and the pressure directly outside the artery at a particular time and at a particular location along the artery. Unlike the pulse pressure, the transmural pressure depends on hydrostatic pressure. For example, if a sensing device is coupled with a wrist of a subject, changing the elevation of the wrist can cause significant changes in the transmural pressure measured at the wrist, while the pulse pressure will generally be relatively unaffected (assuming the state of the subject is otherwise unchanged). As used herein, the term "absolute arterial pressure" refers to the actual pressure in a particular artery at a particular location along the artery at a particular time. Typically, the absolute arterial pressure is relatively consistent with the transmural pressure so long as no significant external pressure is applied to the artery (such as from a counter pressure applied by an inflatable cuff or other external device). For many intents and purposes, the transmural pressure may be presumed to be approximately equal to the absolute arterial pressure, and as such, the terms "absolute arterial pressure" and "transmural pressure" are used interchangeably hereinafter where appropriate unless otherwise noted. As used herein, the term "blood pressure" is a general term referring to a pressure in the arterial system of a subject. As such, the terms transmural pressure, absolute arterial pressure, pulse pressure, systolic pressure and diastolic pressure all may referred to hereinafter generally as blood pressure.

As used herein, the terms "processor," "processing unit," "controller" and "control unit" are used interchangeably and refer to one or more distinct control units or processing units in electrical communication with one another. In some implementations, a processing unit may include one or more of a general purpose single- or multi-chip processor, a central processing unit (CPU), a digital signal processor (DSP), an applications processor, an application specific integrated circuit (ASIC), a field programmable gate array (FPGA) or other programmable logic device (PLD), discrete gate or transistor logic, discrete hardware components, or any combination thereof designed to perform the functions and operations described herein.

As used herein, the terms "device" and "system" are used interchangeably and refer to a physical apparatus that may include a variety of hardware components including discrete logic and other electrical components, as well as components such as computer readable media that may store software or firmware and components such as processors that may execute or otherwise implement software or firmware.

As used herein, the terms "estimating," "calculating," "inferring," "deducing," "evaluating" and "determining" are used interchangeably where appropriate unless otherwise indicated. Similarly, derivations from the roots of these terms may be used interchangeably where appropriate; for example, the terms "estimation," "calculation," "inference" and "determination" may be used interchangeably herein. Additionally, the phrase "capable of" may be used interchangeably with the phrases "configured to," "operable to," "adapted to," "manufactured to," and "programmed to" where appropriate unless otherwise indicated.

Additionally, the conjunction "or" as used herein is intended in the inclusive sense where appropriate unless otherwise indicated; that is, the phrase "A, B or C" is intended to include the possibilities of A individually; B individually; C individually; A and B and not C; B and C and not A; A and C and not B; and A and B and C. Similarly, a phrase referring to "at least one of" a list of items refers to any combination of those items, including single members. As an example, the phrase "at least one of A, B, or C" is intended to cover the possibilities of at least one of A; at least one of B; at least one of C; at least one of A and at least one of B; at least one of B and at least one of C; at least one of A and at least one of C; and at least one of A, at least one of B and at least one of C.

When fluid is injected into a vessel over a relatively short duration of time, the injection will typically generate one or more propagating wave modes of pressure and fluid motion. In the context of the cardiovascular system, propagating wave modes—referred to hereinafter as "pulses"—are generated responsive to the contraction of the left ventricle of the heart and the accompanying injection of blood into the arterial system. The fluid—blood—can be modeled as incompressible, while the vessel—the arterial walls of an artery—can be modeled as elastic. The dominant propagating wave mode along a typical artery is the propagating deformation of the arterial walls of the artery, referred to hereinafter as an arterial distension waveform or as an arterial distension signal (as used herein, the arterial distension signal also can refer to measurements of the arterial distension waveforms obtained for a series or sequence of pulses over an extended duration of time).

The time-varying nature of the arterial distension waveform results from the flow and pressure pulses caused by the subject's heartbeat. As used herein, reference to a pulse can encompass a flow pulse or a pressure pulse—both are physical descriptions of the same underlying response of the arterial system. However, while flow pulses and pressure pulses propagate with the same velocities, the pulse shapes (the particular shapes of the waveforms) of the two types of pulses can generally be different. This difference exists at least in part because of the nonlinear relationship between the arterial distension signal caused by the flow pulses and the time-varying pressure variation associated with the pressure pulses (the difference also can be explained by the complex fluid impedance). The nonlinearity exists in part because the elasticity of the arterial walls decreases with increasing distension. Although the term "arterial distension signal" is sometimes strictly used with reference to flow pulses, as used herein the arterial distension signal may refer to the arterial distension waveform associated with either flow pulses or pressure pulses.

FIG. 1 shows a plot 100 of an example blood pressure signal in an artery versus time during an example cardiac cycle. Although the plot 100 is a plot of blood pressure versus time, the plot 100 also is indicative of the arterial distension waveform. As indicated above, a plot of blood flow (also referred to herein as "arterial flow") versus time would exhibit similar features as the plot 100 of blood pressure versus time, although the specific shapes of the features would be slightly different. As a person of ordinary skill in the art will appreciate, each cardiac cycle 102 includes both a systolic phase ("ventricular systole") 104, during which the left ventricle of the heart contracts and pumps blood into the arterial system, and a diastolic phase ("ventricular diastole") 106, during which the left ventricle relaxes and fills with blood in preparation for the next systolic phase. Because each cardiac cycle 102 yields a respective pressure pulse, the arterial distension waveform associated with each pressure pulse also includes features characteristic of the systolic and diastolic phases. For example, the systolic phase 104 characteristically includes a rapid rise of the pressure culminating in a local maximum or peak 108 (the "systolic pressure") responsive to the injection of blood from the left ventricle during the given cardiac cycle 102. The diastolic phase 106, on the contrary, characteristically includes a marked drop in blood pressure culminating in a local minimum 110 (the "diastolic pressure") during the given cardiac cycle 102 as a consequence of the relaxation of the left ventricle. In fact, the ending portion of the diastolic phase 106 can be characterized by an exponentially decaying blood pressure that asymptotically approaches a pressure 112 (referred to herein as the "infinity pressure") lower than the typical diastolic pressure (the blood pressure never reaches the infinity pressure because the systolic phase of the next cardiac cycle interrupts the exponential decay as shown).

Figure 2:
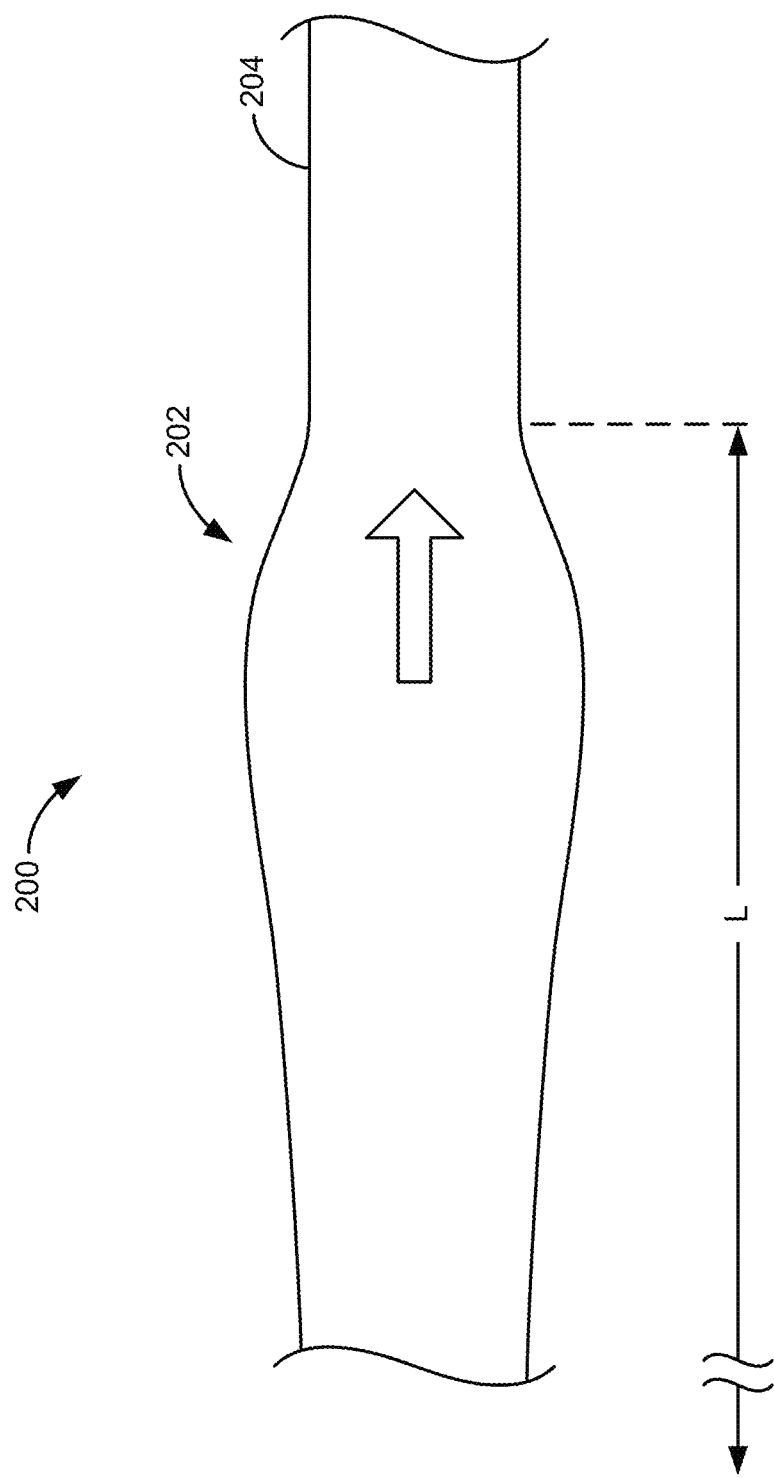
FIG. 2 shows a cross-sectional side view of a diagrammatic representation of a portion of an artery through which a pressure pulse is propagating.

FIG. 2 shows a cross-sectional side view of a diagrammatic representation of a portion of an artery 200 through which a pressure pulse 202 is propagating. The block arrow in FIG. 2 shows the direction of blood flow and pulse propagation. As diagrammatically shown, the propagating pulse 202 causes strain in the arterial walls 204, which is manifested in the form of an enlargement in the diameter (and consequently the cross-sectional area A) of the arterial walls—referred to as "distension." The spatial length L of an actual propagating pulse along an artery (along the direction of blood flow) is typically comparable to the length of a limb, such as the distance from a subject's shoulder to the subject's wrist or finger, and is generally less than one meter (m). The spatial length L of a pulse will generally decrease with increasing distance from the heart until the pulse reaches capillaries. However, the length L of a propagating pulse can vary considerably from subject to subject, and for a given subject, can vary significantly over durations of time depending on various factors.

Figure 3:
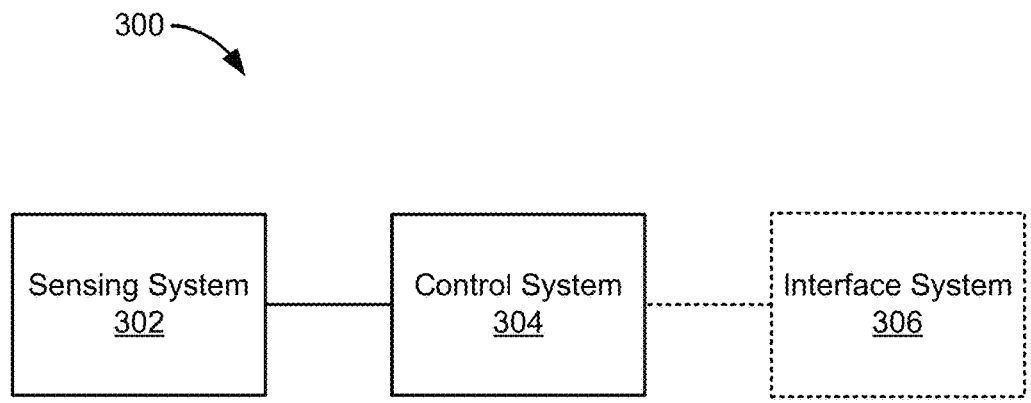
FIG. 3 shows a block diagram representation of an example biological signal monitoring system according to some implementations.

FIG. 3 shows a block diagram representation of an example biological signal monitoring system 300 according to some implementations. As shown, the monitoring system 300 includes a sensing system 302 and a control system 304 electrically coupled with the sensing system. The sensing system 302 is capable of performing measurements associated with one or more signals or quantities of interest and providing raw sensor data, including raw arterial data, based on the measurements. The control system 304 is capable of controlling operation of the sensing system 302 and processing sensor data received from the sensor system. In some implementations, the monitoring system 300 further includes an interface system 306 capable of transmitting or receiving data, such as raw or processed sensor data, to or from various components within or integrated with the monitoring system 300 or, in some implementations, to or from various components, devices or other systems external to the monitoring system 300.

Figure 4:
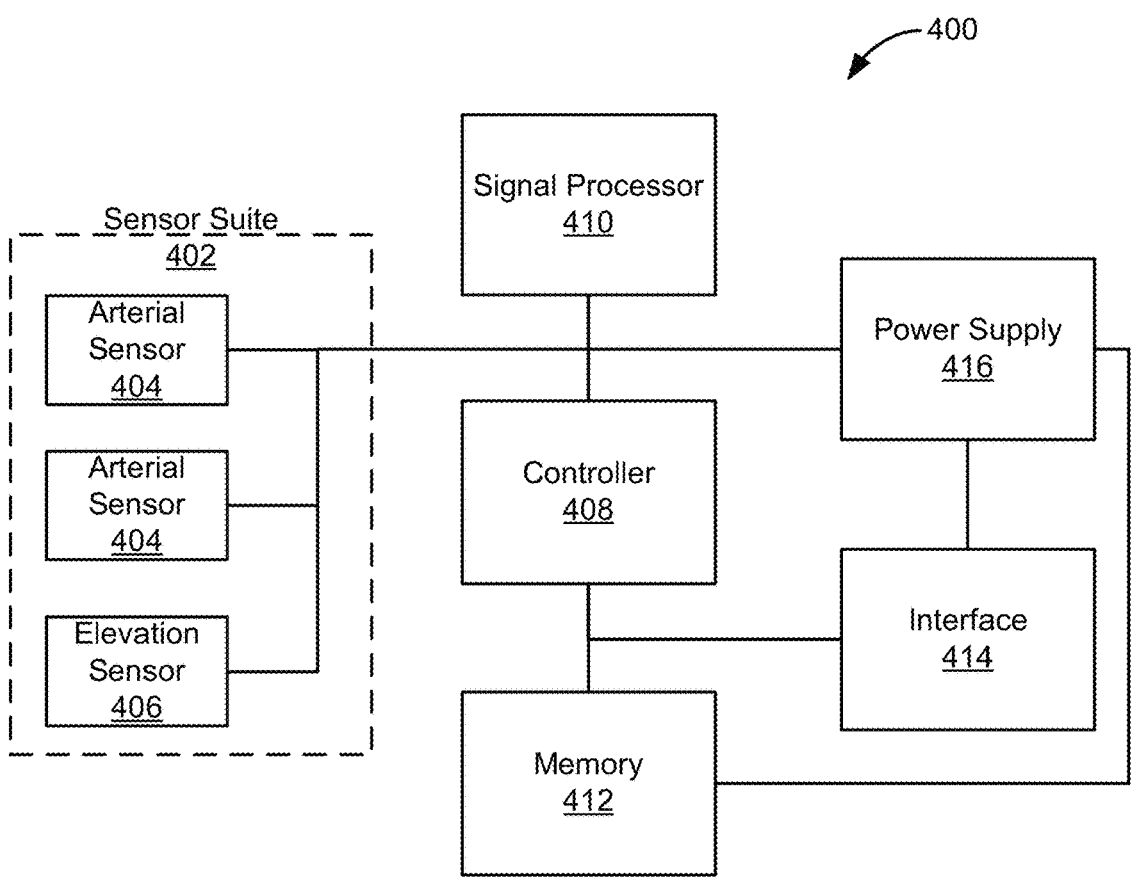
FIG. 4 shows a block diagram representation of an example blood pressure estimation device according to some implementations.

FIG. 4 shows a block diagram representation of an example blood pressure estimation device 400 according to some implementations. The blood pressure estimation device 400 is an example implementation of the biological signal monitoring system 300 described above with reference to FIG. 3. For example, the blood pressure estimation device 400 includes a sensor suite 402 that implements the sensing system 302 of FIG. 3. The sensor suite 402 includes at least one arterial sensor 404. In some implementations, the sensor suite 402 includes two or more arterial sensors 404 of the same sensor type (modality). In some implementations, the sensor suite 402 includes two or more arterial sensors 404 of different sensor types (modalities). In some implementations, the sensor suite 402 includes an arterial sensor 404 configured for ultrasonic sensing. Additionally or alternatively, the sensor suite 402 can include an arterial sensor 404 configured for optical sensing. Additionally or alternatively, the sensor suite 402 can include an arterial sensor 404 configured for impedance plethysmography (IPG) sensing, also referred to in biological contexts as bioimpedance sensing.

In various implementations, whatever type or types of sensor modality are utilized, each arterial sensor 404 broadly functions to obtain measurements (also referred to as "arterial data"). Such arterial data can include arterial distension data indicative of an arterial distension signal resulting from the propagation of pulses through a portion of the artery proximate to the arterial sensor 404. In some implementations, an arterial sensor 404 can be configured to provide an output that may be continuously converted to a measure of the arterial distension $\delta A$ as a function of time (also referred to herein as "arterial distension data" or "arterial distension measurements"). Additionally or alternatively, in some implementations, the same or a different arterial sensor 404 can be configured to provide the same or a different output that may be continuously converted to a measure of the arterial cross-sectional area A as a function of time (also referred to herein as ("arterial cross-sectional area data," "cross-sectional area measurements,"). Additionally or alternatively, in some implementations, the same or a different arterial sensor 404 can be configured to provide the same or a different output that may be continuously converted to a measure of the blood velocity v as a function of time (also referred to herein as "blood velocity data" or "blood velocity measurements"). Additionally or alternatively, in some implementations, the same or a different arterial sensor 404 can be configured to provide the same or a different output that may be continuously converted to a measure of the blood flow Q as a function of time (also referred to herein as "blood flow data" or "blood flow measurements"). In some implementations, the arterial data measured or otherwise obtained by the arterial sensor 404 can be provided to the controller 408 in the form of an electrical signal such as a voltage signal.

Referring back to FIG. 4, the sensor suite 402 also can include an elevation sensor 406 for determining an elevation (also used interchangeably with and referred to as a "height") of the device. In some implementations, the elevation can be a differential elevation relative to a previous elevation, a differential elevation relative to a reference elevation, or an absolute elevation (or altitude). In various implementations, the elevation sensor 406 can collectively refer to one or more of each of a plurality of different types of sensors. For example, the elevation sensor 406 can include one or more accelerometers or one or more gyroscopes for detecting relative motion and orientation. For example, the one or more accelerometers can include a three-dimensional (3D) inertial sensor, such as a three-axis accelerometer. Elevation changes may be inferred from integration of the accelerometer output. In some implementations, the position and elevation of the blood pressure estimation device 400 can be tracked using such sensors. In some such implementations, the elevation sensor 406 can be configured to provide an output that may be continuously converted to a measure of the elevation of the blood pressure estimation device 400 as a function of time (also referred to herein as "elevation data" or "elevation measurements"). Additionally or alternatively, the elevation sensor 406 can include an absolute elevation sensor such as a high resolution barometric altimeter. Additionally or alternatively, a magnetic near-field navigation system can be integrated in the blood pressure estimation device 400 to provide elevation estimates.

In the blood pressure estimation device 400, the control system 304 is implemented at least in part by a controller 408. The controller 408 is electrically coupled with the sensor suite 402. The controller 408 is capable of processing the arterial data received from the arterial sensors 404 and the elevation data received from the elevation sensor 406. While the controller 408 is shown and described as a single component, in some implementations, the controller 408 can collectively refer to two or more distinct control units or processing units in electrical communication with one another. In some implementations, the controller 408 includes one or more of a general purpose single- or multi-chip processor, a central processing unit (CPU), a digital signal processor (DSP), an application specific integrated circuit (ASIC), a field programmable gate array (FPGA) or other programmable logic device (PLD), discrete gate or transistor logic, discrete hardware components, or any combination thereof designed to perform the functions and operations described herein.

In some implementations, the blood pressure estimation device 400 further includes a signal processor 410. In some implementations, raw sensor data including raw arterial data and raw elevation data, can be sent, transmitted, communicated or otherwise provided to the signal processor 410 from the sensor suite 402 or from the controller 408. For example, the signal processor 410 can include any suitable combination of hardware, firmware and software configured, adapted or otherwise operable to detect, extract and otherwise process or determine an arterial distension signal, blood flow signal or other signals of interest based on the raw arterial data received from the sensor suite 402. In some implementations, the signal processor 410 can include signal or image processing circuits or circuit components including, for example, amplifiers (such as instrumentation amplifiers), analog or digital mixers or multipliers, switches, analog-to-digital converters (ADCs), passive or active analog filters, among others. In some implementations, the signal processor 410 can be integrated with or within the controller 408, for example, where the controller 408 is implemented as a system-on-chip (SoC) or system-in-package (SIP). In some implementations, the signal processor 410 can be a DSP included within or otherwise coupled with the controller 408. In some implementations, the signal processor 410 can be implemented at least partially via software. For example, one or more functions of, or operations performed by, one or more of the circuits or circuit components just described can instead be performed by one or more software modules executing, for example, in a processing unit of the controller 408 (such as in a general purpose processor or a DSP).

In some implementations, raw arterial distension data obtained by the arterial sensor 404 is advantageously processed using high-pass filtering techniques. In some such implementations, the signal processor 410 performs one or more high-pass filtering operations on the raw arterial distension data using, for example, one or more analog or digital filtering operations performed via any suitable combination of software and hardware including digital or discrete components, and in some instances, one or more passive or active filter components. Such high-pass filtering can advantageously be used to significantly reduce low spectral frequency components, for example, having frequencies below a few Hertz (Hz) (for example, below 3 Hz or below 4 Hz). Such low spectral frequency components can be caused by motion artifacts, respiration artifacts or from low frequency propagating waves not of interest.

In some implementations, the arterial data also can be advantageously processed using low-pass filtering techniques or bandpass filtering techniques. In some such implementations, the signal processor 410 performs one or more low-pass filtering operations on the arterial distension data using, for example, one or more analog or digital filtering operations performed via any suitable combination of software and hardware including digital or discrete components, and in some instances, one or more passive or active filter components. Such low-pass filtering can advantageously be used to significantly reduce high frequency noise components outside of the frequency band of interest.

The controller 408 can store data in, and retrieve data from, a memory 412. For example, the data stored in the memory 412 can include raw arterial data and elevation data obtained from one or more sensors of the sensor suite 402, filtered or otherwise processed arterial data or elevation data, or calculated or estimated cardiovascular characteristics or signals, such as blood pressure, determined based on such raw or processed arterial distension data and elevation data. The memory 412 also can store processor-executable code or other executable computer-readable instructions capable of execution by the controller 408 to perform various operations (or to cause other components such as sensors in the sensor suite 402 or the signal processor 410 to perform operations), including any of the calculations, computations, estimations or other determinations described herein (including those presented in any of the equations below). It should also be understood that the memory 412 can collectively refer to one or more memory devices (or "components"). For example, depending on the implementation, the controller 408 can have access to and store data in a different memory device than the signal processor 410. In some implementations, one or more of the memory components can be implemented as a NOR- or NAND-based Flash memory array. In some other implementations, one or more of the memory components can be implemented as a different type of non-volatile memory. Additionally, in some implementations, one or more of the memory components can include a volatile memory array such as, for example, a type of RAM.

In some implementations, the controller 408 can communicate data stored in the memory 412 or data received directly from the signal processor 410 through an interface 414. For example, such communicated data can include blood pressure data or other data derived or otherwise determined from the arterial data or the elevation data. The interface 414 can collectively refer to one or more interfaces of one or more various types. In some implementations, the interface 414 can include a memory interface for receiving data from or storing data to an external memory such as a removable memory device. Additionally or alternatively, the interface 414 can include one or more wireless network interfaces or one or more wired network interfaces enabling the transfer of raw or processed data to, as well as the reception of data from, an external computing device, system or server.

A power supply 416 can provide power to some or all of the components in the blood pressure estimation device 400. The power supply 416 can include one or more of a variety of energy storage devices. For example, the power supply 416 can include a rechargeable battery, such as a nickel-cadmium battery or a lithium-ion battery. Additionally or alternatively, the power supply 416 can include one or more supercapacitors. In some implementations, the power supply 416 can be chargeable (or "rechargeable") using power accessed from, for example, a wall socket (or "outlet") or a photovoltaic device (or "solar cell" or "solar cell array") integrated with the blood pressure estimation device 400. Additionally or alternatively, the power supply 416 can be wirelessly chargeable.

The aforedescribed components of the blood pressure estimation device 400 can be configured in a single housing. The housing and other components of the blood pressure estimation device 400 can be configured such that when the monitoring device is affixed or otherwise physically coupled to a subject, the arterial sensor 404 is in contact with or in close proximity to the skin of the user. In various implementations, the housing of the blood pressure estimation device 400 is a wearable housing or is incorporated into or integrated with a wearable housing. In some specific implementations, the wearable housing includes (or is connected with) a physical coupling mechanism for removable noninvasive attachment to the user. The housing can be formed using any of a variety of suitable manufacturing processes, including injection molding and vacuum forming, among others. In addition, the housing can be made from any of a variety of suitable materials, including, but not limited to, plastic, metal, glass, rubber and ceramic, or combinations of these or other materials. In particular implementations, the housing and coupling mechanism enable full ambulatory use. In other words, some implementations of the blood pressure estimation devices described herein are noninvasive, not physically-inhibiting and generally do not restrict the free uninhibited motion of a subject's arms or legs, enabling continuous or periodic monitoring of cardiovascular characteristics such as blood pressure even as the subject is mobile or otherwise engaged in a physical activity. As such, the ambulatory blood pressure estimation device 400 facilitates and enables long-term wearing and monitoring (for example, over days, weeks or a month or more without interruption) of one or more biological characteristics of interest to obtain a better picture of such characteristics over extended durations of time, and generally, a better picture of the user's health.

Figure 5A:
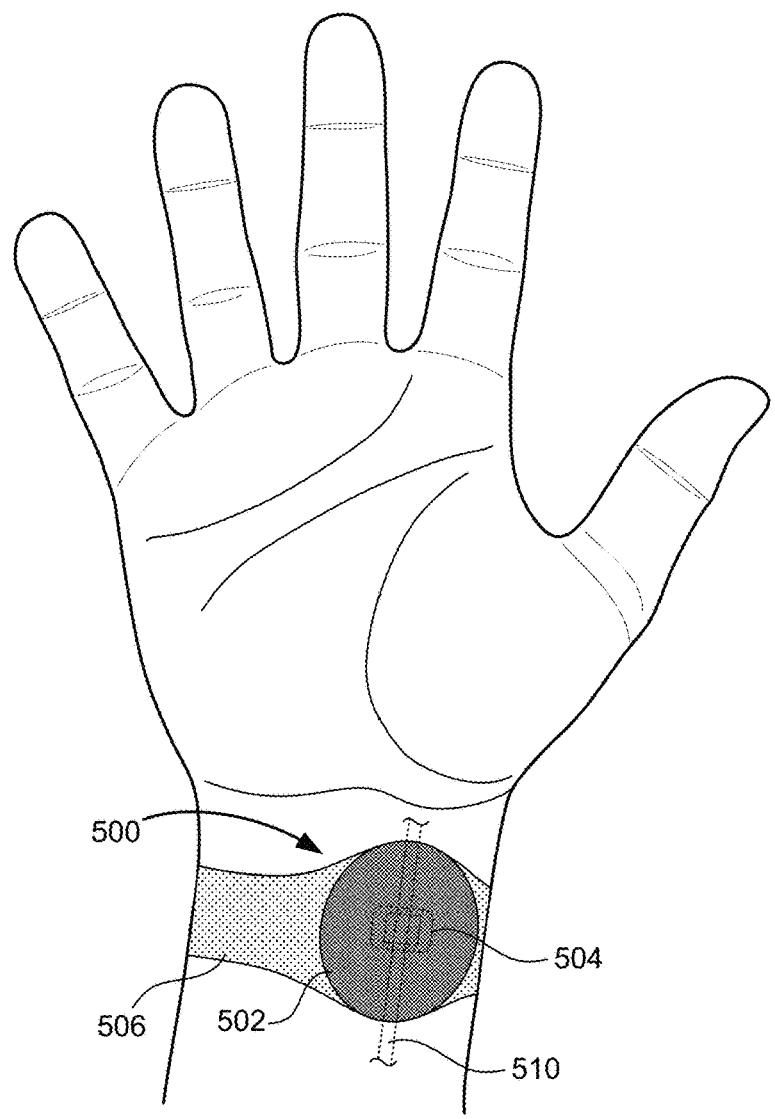
FIG. 5A shows an example blood pressure estimation device designed to be worn around a wrist according to some implementations.

In some implementations, the blood pressure estimation device 400 can be positioned around a wrist of a user with a flexible or elastic strap or band. FIG. 5A shows an example blood pressure estimation device 500 designed to be worn around a wrist according to some implementations. In the illustrated example, the blood pressure estimation device 500 includes a housing 502 integrally formed with, coupled with or otherwise integrated with a wristband 506. During operation, the blood pressure estimation device 500 can be coupled around the wrist such that arterial sensor (or sensors) 504 are positioned along a segment of the radial artery 510. In some implementations, the arterial sensor 504 may be hidden from view from the external or outer surface of the housing 502 facing the subject while the blood pressure estimation device 500 is coupled with the subject, but exposed on an inner surface of the housing 502 to enable the arterial sensor 504 to obtain measurements through the subject's skin from the underlying artery. In some other implementations, the blood pressure estimation device 500 can similarly be designed or adapted for positioning around a forearm, an upper arm, an ankle, a lower leg, an upper leg, or a finger (all of which are hereinafter referred to as "limbs") using a strap or band.

Figure 5B:
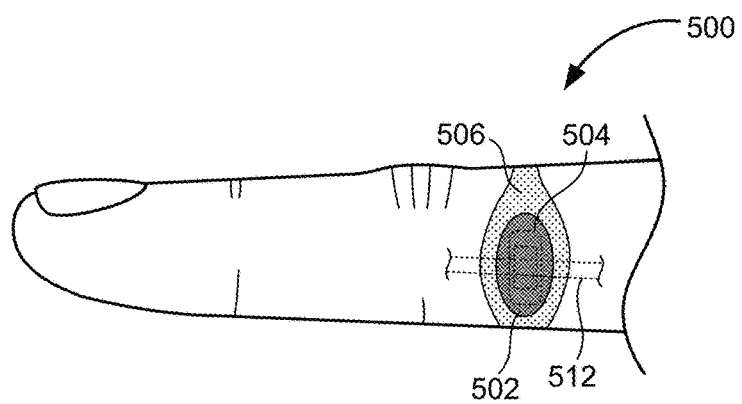
FIG. 5B shows an example blood pressure estimation device designed to be worn around a finger according to some implementations.

In some other implementations, the blood pressure estimation devices disclosed herein can be positioned on a region of interest of the user without the use of a strap or band. For example, the arterial sensor 504 and the other components of the blood pressure estimation device 500 can be enclosed in a housing that is secured to the skin of the user using an adhesive or other suitable attachment mechanism (an example of a "patch" device). FIG. 5B shows an example blood pressure estimation device 500 designed to be worn around a finger according to some implementations.

In some such implementations, the blood pressure estimation device 500 can be coupled around the finger such that arterial sensor 504 is positioned along a segment of the digital artery 512.

Figure 6A:
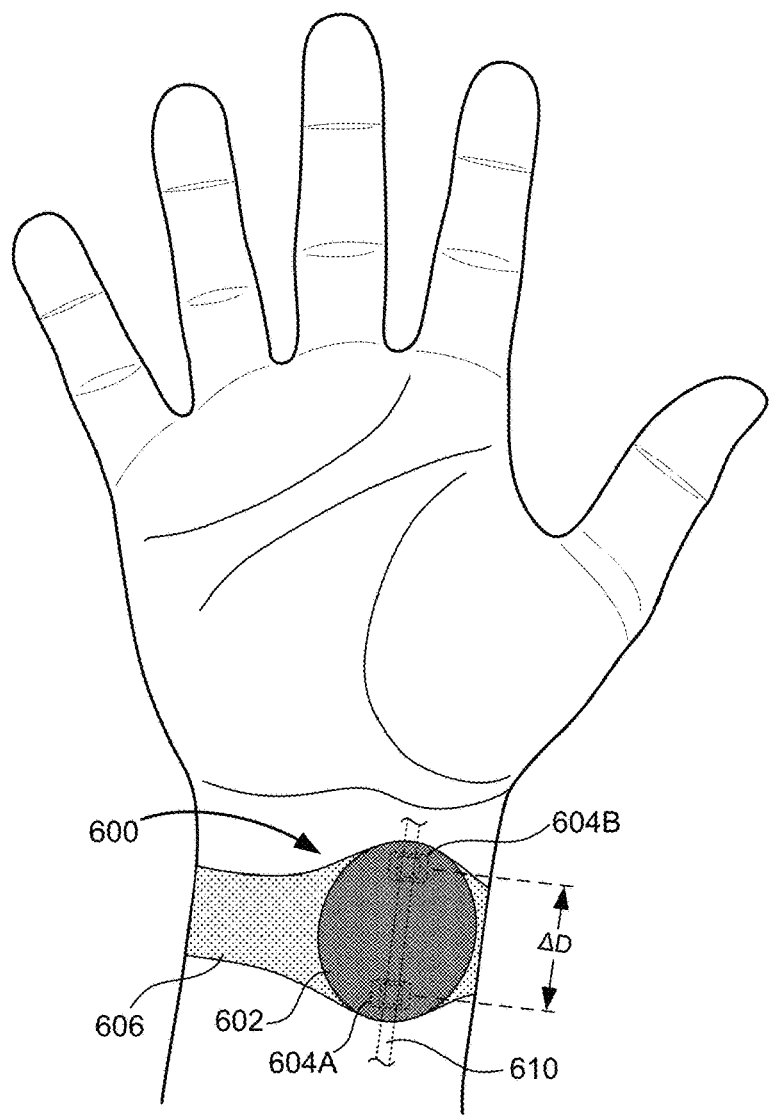
FIG. 6A shows an example multi-sensor blood pressure estimation device designed to be worn around a wrist according to some implementations.

FIG. 6A shows an example multi-sensor blood pressure estimation device 600 designed to be worn around a wrist according to some implementations. In some implementations, the multi-sensor blood pressure estimation device 600 includes at least two arterial sensors including a first arterial sensor 604A and a second arterial sensor 604B. In some implementations, both the first arterial sensor 604A and the second arterial sensor 604B are sensors of the same sensor type. In some such implementations, the first arterial sensor 604A and the second arterial sensor 604B are identical sensors. In such implementations, each of the first arterial sensor 604A and the second arterial sensor 604B utilizes the same sensor technology with the same sensitivity to the arterial distension signal caused by the propagating pulses, and has the same time delays and sampling characteristics.

Figure 6B:
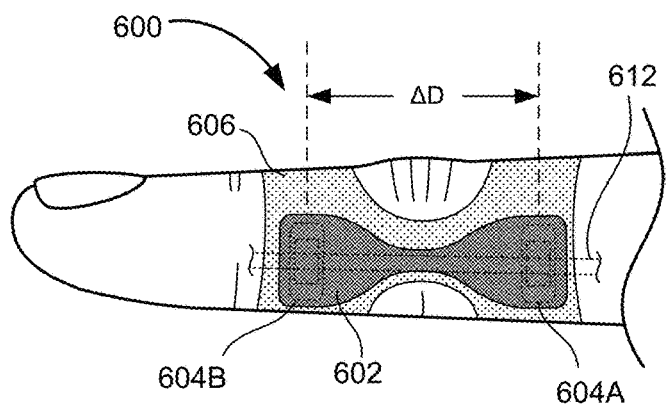
FIG. 6B shows an example multi-sensor blood pressure estimation device designed to be worn around a finger according to some implementations.

The blood pressure estimation device 600 also includes a housing 602 integrally formed with, coupled with or otherwise integrated with a wristband 606. During operation, the blood pressure estimation device 600 can be coupled around the wrist such that the first and the second arterial sensors 604A and 604B are positioned along a segment of the radial artery 610. Again, in some implementations, the first and the second arterial sensors 604A and 604B may be hidden from view from the external or outer surface of the housing 602 facing the subject, but exposed on an inner surface of the housing 602. In some other implementations, the blood pressure estimation device 600 can similarly be designed or adapted for positioning around another limb using a strap or band. FIG. 6B shows an example multi-sensor blood pressure estimation device 600 designed to be worn around a finger according to some implementations. Like the blood pressure estimation device 500 of FIG. 5B, the blood pressure estimation device 600 can be coupled around the finger such that arterial sensors 604A and 604B are positioned along a segment of the digital artery 612.

In some implementations, the magnitude of the distance $\Delta D$ of separation between the first arterial sensor 604A and the second arterial sensor 604B (and consequently the distance between the first and the second locations along the artery during regular operation) can be in the range of about 1 centimeter (cm) to tens of centimeters—long enough to distinguish the arrival of the pulse at the first physical location from the arrival of the pulse at the second physical location, but close enough to provide sufficient assurance of arterial consistency. In some specific implementations, the distance $\Delta D$ between the first and the second arterial distension sensors 604A and 604B can be in the range of about 1 cm to about 30 cm, and in some implementations, less than or equal to about 20 cm, and in some implementations, less than or equal to about 10 cm, and in some specific implementations less than or equal to about 5 cm. In some other implementations, the distance $\Delta D$ between the first and the second arterial distension sensors 604A and 604B can be less than or equal to 1 cm, for example, about 0.1 cm, about 0.25 cm, about 0.5 cm or about 0.75 cm. By way of reference, a typical PWV can be about 15 meters per second (m/s). Using an blood pressure estimation device 600 in which the first and the second arterial distension sensors 604A and 604B are separated by a distance of about 5 cm, and assuming a PWV of about 15 m/s implies a PTT of approximately 3.3 milliseconds (ms). As will be appreciated by a person of ordinary skill in the art, the spatial length L of a pulse can be greater than the distance $\Delta D$ from the first arterial distension sensor 604A to the second arterial sensor 604B in such implementations. The value of the magnitude of the distance $\Delta D$ between the first and the second arterial sensors 604A and 604B can be preprogrammed into or otherwise stored in the memory 412.

As described above, during the systolic phase of the cardiac cycle, as a pulse propagates through a particular location along an artery, the arterial walls expand according to the pulse waveform and the elastic properties of the arterial walls. Along with the expansion is a corresponding increase in the volume of blood at the particular location or region, and with the increase in volume of blood an associated change in one or more characteristics in the region. Conversely, during the diastolic phase of the cardiac cycle, the blood pressure in the arteries decreases and the arterial walls contract. Along with the contraction is a corresponding decrease in the volume of blood at the particular location, and with the decrease in volume of blood an associated change in the one or more characteristics in the region.

In the context of bioimpedance sensing (or impedance plethysmography (IPG)), the blood in the arteries has a greater electrical conductivity than that of the surrounding or adjacent skin, muscle, fat, tendons, ligaments, bone, lymph or other tissues. The susceptance (and thus the permittivity) of blood also is different from the susceptances (and permittivities) of the other types of surrounding or nearby tissues. As a pulse propagates through a particular location, the corresponding increase in the volume of blood results in an increase in the electrical conductivity at the particular location (and more generally an increase in the admittance, or equivalently a decrease in the impedance). Conversely, during the diastolic phase of the cardiac cycle, the corresponding decrease in the volume of blood results in an increase in the electrical resistivity at the particular location (and more generally an increase in the impedance, or equivalently a decrease in the admittance).

Figure 7:
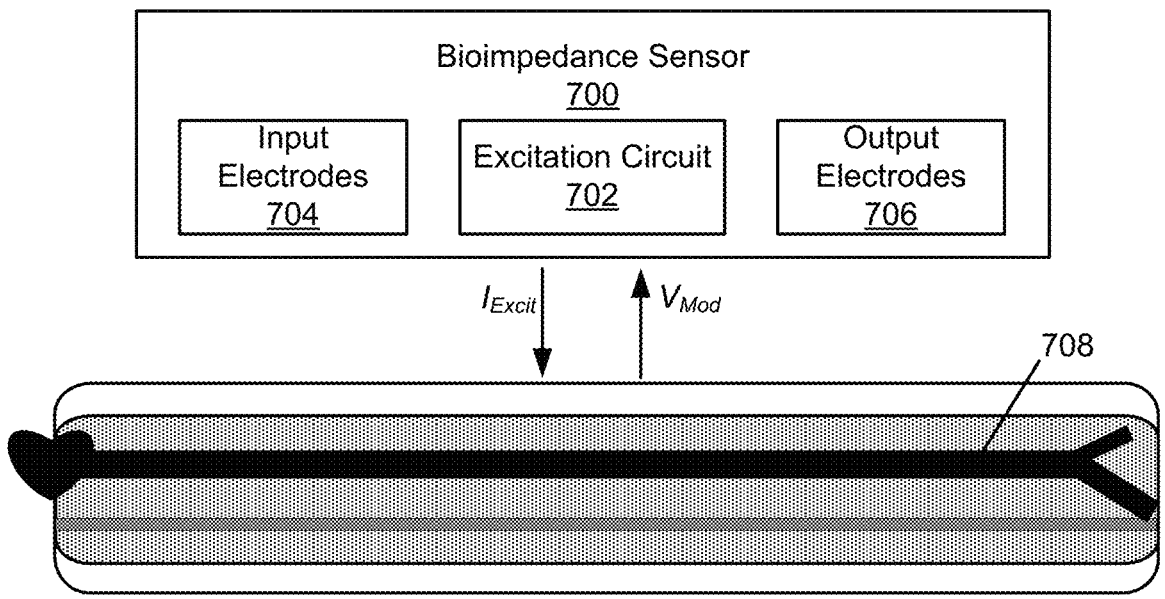
FIG. 7 shows a block diagram representation of an example bioimpedance sensor according to some implementations.

An arterial sensor 404 configured as a bioimpedance sensor generally functions to perform measurements by applying an electrical excitation signal at an excitation carrier frequency to a region of interest via two or more input electrodes, and by detecting an output signal (or output signals) via two or more output electrodes. FIG. 7 shows a block diagram representation of an example bioimpedance sensor 700 according to some implementations. The bioimpedance sensor 700 includes an excitation circuit 702 capable of generating an electrical excitation signal $I_{Excit}$ having an adjustable excitation frequency $f_{Excit}$ (in some other implementations, the excitation circuit 702 can be implemented in or integrated with a controller, for example, the controller 408). In some implementations, the excitation circuit 702 can simultaneously or alternately generate multiple excitation signals at different excitation frequencies depending on the biological characteristics of interest. In the illustrated implementation, the excitation circuit 702 functions as a current source that provides the excitation signal $I_{Excit}$ in the form of an electrical current signal, and more specifically, a radio frequency (RF) alternating current (AC) signal. In some implementations, the excitation circuit 702 can include a current mirror comprised of a multiple MOSFETs or bipolar junction transistors as well as other circuit components such as amplifiers.

The excitation signal $I_{Excit}$ is injected into (or "provided to") the artery 708 of interest via two or more of input electrodes 704 in contact with the skin of the subject overlying the artery. The injected excitation signal $I_{Excit}$ can be a single-ended signal or a differential signal. The bioimpedance sensor 700 also includes one or more output electrodes 706 in contact with the skin in proximity to the artery 708 of interest. The output electrodes 706 are operable to sense a voltage response signal $V_{Mod}$. In some such implementations, the voltage response signal $V_{Mod}$ is representative of an electrical voltage response of the tissues including the blood in the artery 708 of interest to the applied excitation signal $I_{Excit}$. The detected voltage response signal $V_{Mod}$ is influenced by the different, and in some instances time-varying, electrical properties of the various tissues through which the injected excitation current signal is passed. The detected voltage response signal $V_{Mod}$ is amplitude- and phase-modulated by the time-varying impedance (or inversely the admittance) of the underlying artery 708, which fluctuates synchronously with the user's heartbeat. To determine various biological characteristics, information in the detected voltage response signal is generally demodulated from the excitation carrier frequency component of the detected voltage response signal $V_{Mod}$.

In the context of optical sensing, the absorbance or scattering of some frequencies of light (for example, within the near-infrared (NIR) window) by the blood or by various components of the blood (for example, red blood cells) in the arteries is different than that of the surrounding or adjacent skin, muscle, fat, tendons, ligaments, bone, lymph or other tissues. For example, and as similarly described above, as a pulse propagates through a particular location of an artery, the corresponding increase in the volume of blood can result in an increase in the absorption of particular frequencies of light at the particular location. Some arterial sensors 404 configured as an optical sensor generally functions to perform measurements by applying an optical signal (electromagnetic radiation) at a transmitter frequency to a region of interest via one or more light emitters, and by detecting a backscattered or reflected signal (or signals) via one or more light detectors.

Figure 8:
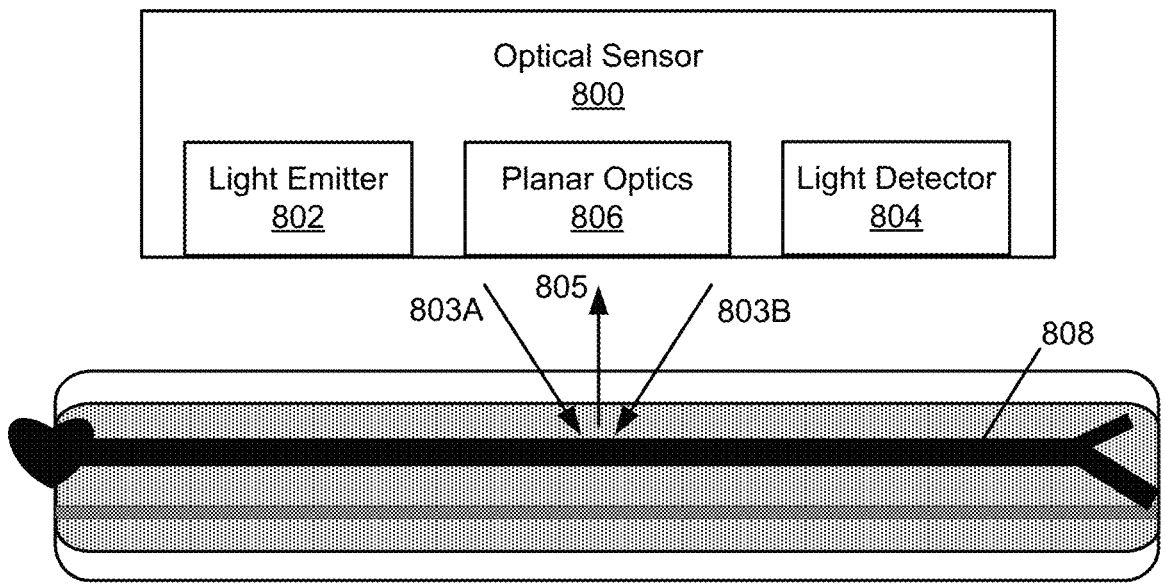
FIG. 8 shows a block diagram representation of an example optical sensor according to some implementations.

FIG. 8 shows a block diagram representation of an example optical sensor 800 according to some implementations. For example, the optical sensor 800 can implement one or more of the arterial sensors 404 of the blood pressure estimation device 400. In some implementations, the optical sensor 800 can be structured as a planar device configured to be arranged flush with, or at least parallel to, the skin surface of a limb. In some implementations, the optical sensor 800 is configured as a Doppler velocimetry sensor, such as a laser Doppler velocimetry (LDV) sensor. Using a Doppler velocimetry sensor, such as an LDV sensor, to implement the optical sensor 800 enables the measurement of the velocity v of blood flowing parallel to the skin, as is the case in most arteries in limbs and digits. An LDV sensor also can distinguish flowing blood from other tissues, and thus enable the obtainment of the arterial lumen V in the same measurement. Having both the velocity v and the arterial lumen V then enables a determination of the blood flow Q through the artery.

The optical sensor 800 may include one or more light emitters 802 (also referred to herein collectively as "the light emitter," "the light transmitter" or "the light source"). In some implementations, the light emitter 802 is configured to emit coherent light. In some such implementations, the light emitter 802 includes one or more lasers, such as laser diodes. In some implementations, the light emitter 802 may be configured to emit light of a wavelength that is less susceptible to absorption by biological tissue and water. In some implementations, the light emitter 802 can include a laser, such as an edge emitting semiconductor laser or a vertical cavity surface emitting laser (VCSEL) that produces a light beam having an infrared wavelength in the range of 850 nanometers (nm) to 1500 nm. In some other implementations, the light emitter 802 can emit light beams having visible wavelengths.

The optical sensor 800 also includes one or more light detectors 804 (also referred to herein collectively as "the light detector" or "the photodetector"). In some implementations, the light detector 804 includes one or more photodiode arrays. In some implementations, the light detector 804 may be configured to detect backscattered light of a particular range of wavelengths. For example, a silicon (Si) photodiode may be used to detect wavelengths of light below 900 nm, a germanium (Ge) photodiode may be used to detect wavelengths up to 1300 nm, and a gallium arsenide (GaAs) photodiode or Indium phosphide (InP) photodiode may be used to detect light of longer wavelengths. The light detector 804 may receive backscattered light and convert the received light power of the backscattered light to an electrical output signal. The electrical output signal of the light detector 804 may be converted to a voltage signal by a transimpedance amplifier (not shown).

In some implementations, the optical sensor 800 includes one or more planar optical structures 806 (collectively referred to hereinafter as "planar optics") configured to direct optical light emitted from the light emitter 802 into two light beams 803A and 803B. In some implementations, the planar optics also can be configured to collect and shunt backscattered light 805 to the light detector 804. In some implementations, the planar optics 806 can include a planar transparent structure having refractive index structures, surface relief structures, diffractive structures, or other waveguide structures known in the art to direct the light from the light emitter 802 out of the optical sensor 800 and to collect and direct backscattered light towards the light detector 804. In some implementations, the planar optics 806 are configured as a waveguide having a diffractive structure comprised of two superimposed gratings. The superimposed gratings can be configured to have slightly different grating constants and a mean grating constant approximately equal to the optical wavelength of the light emitter 802. In implementations in which the optical sensor 800 is implemented as an LDV, the two light beams 803A and 803B output by the light emitter 802 are directed so that the beams have different directions of propagation and intersect to form an interference pattern that propagates perpendicularly away from the surface of the waveguide. In some implementations, the light emitter 802 and planar optics 806 may be configured to direct the two light beams 803A and 803B into the subject's limb towards an artery 808 to illuminate the artery with an interference pattern forming a measurement volume that includes a cross-section of the artery.

Figure 9:
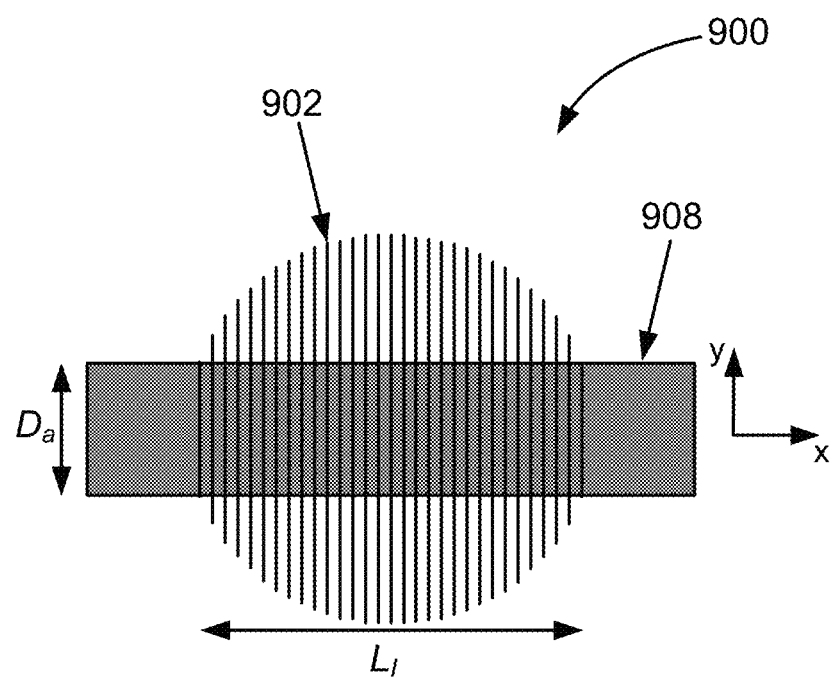
FIG. 9 shows a cross-section of an example measurement volume in which an interference pattern is illuminating an artery according to some implementations.

FIG. 9 shows a cross-section of an example measurement volume 900 in which an interference pattern 902 is illuminating an artery 908 according to some implementations. In the illustrated implementation, the interference pattern 902 of the measurement volume 900 includes a number of interference fringes that are parallel to the bisector of the axes of the two emitted beams and transverse an arterial longitudinal axis of the artery 908. In some examples, the interference fringes may be perpendicular to the arterial longitudinal axis of the artery 908, or approximately perpendicular to the arterial longitudinal axis of the artery 908. The spacing between the fringes, or "fringe spacing," may be determined by the optical wavelength of, and the angle between, the emitted beams that form the interference pattern 902. In some implementations, the fringe spacing is larger than the typical diameter $D_a$ of blood cells (approximately 10 μm). The number of fringes may, in some instances, be limited according to the length $L_1$ of the illuminated area. In some example implementations, the interference pattern may include between 5 fringes and 100 fringes, for example 20 fringes. In the example shown in FIG. 9, the illustrated segment of the artery 908 is substantially straight, with an arterial longitudinal axis that corresponds with an x axis. In this example, the transverse or perpendicular axis corresponds with a y axis.

As described above, the two light beams 803A and 803B output by the light emitter 802 propagate into the tissues perpendicular to the long axis of the artery 808 beneath the skin. The measurement of velocity in an artery that is perpendicular to the overall direction of propagation of light is possible because the interference fringes are aligned in the same direction as the direction of the bisector of the two transmitted beams 803A and 803B. The light scattered by moving blood cells will then be frequency-modulated and the modulation frequency $f_d$ will be given by the velocity v of the moving blood cells in conjunction with the spacing between interference fringes. This may be expressed as $$f_d = \frac{v}{\lambda/2\sin(\alpha)},$$

where $\lambda$ represents the optical wavelength and $2\alpha$ represents the angle between the two transmitted beams 803A and 803B. Because the two beams 803A and 803B either originate from the same light source or at least from two mutually coherent light sources, and also are assumed to have the same optical path length from the source (at least within the coherence length of the source), the two beams form an interference pattern in the intersection region with interference fringes aligned in the direction of the bisector of the beams and at a fringe spacing of $x_f=\lambda/(2 \sin \alpha)$, where $\alpha$ is half the angle between the two light beams.

A particle such as a red blood cell moving through the interference pattern with a velocity component $v_x$ in the plane of the intersecting beams and perpendicular to the bisector of the light beams will scatter light modulated by a frequency given by the dot product of the velocity v and a vector defining the difference between the propagation vectors of the two beams divided by $2\pi$, i.e., $\Delta f=v_x/x_f=v\cdot\Delta k/2\pi$ where $\Delta f$ is the Doppler frequency shift observed in back-scattered light, $v_x$ is the velocity component perpendicular to the propagation direction of light, $x_f$ is the fringe spacing of the interference pattern formed in the measurement volume, and the vector $\Delta k$ is the difference between the propagation vectors of the two light beams 803A and 803B. The difference of the Doppler shifts of scattered light in a given direction (arbitrary) emerging from the two impinging beams will be independent of the scattering direction (direction of detection). The frequency shift $\Delta f$ observed in the backscattered light received by the light detector 804 is proportional to the velocity component of backscattering particles perpendicular to the bisector of the two beams 803A and 803B.

Figure 10:
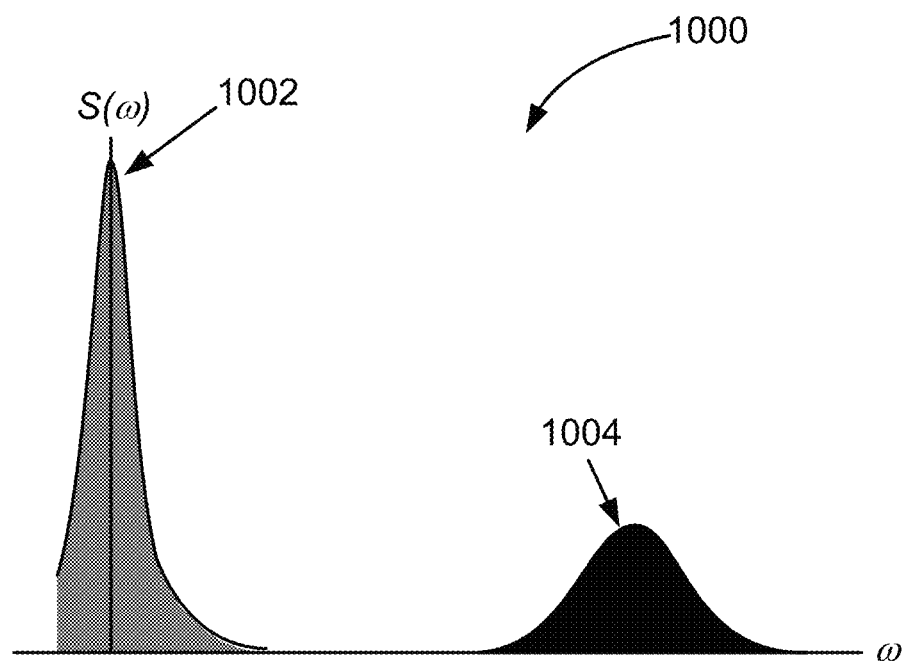
FIG. 10 shows a plot of a power spectrum of an example output signal output by the light detector of FIG. 8.

FIG. 10 shows a plot of a power spectrum 1000 of an example output signal output by the light detector 804 of FIG. 8. In particular, FIG. 10 shows a plot of the magnitude S of the detected light signal, which is proportional to backscattered light intensity, versus frequency ω. As shown, the power spectrum 1000 includes a non-shifted portion or peak 1002 and a frequency-shifted portion or peak 1004. The frequency-shifted portion 1004 corresponds to the power (or intensity) of received light due to backscattering by moving particles (blood cells) moving through the interference pattern of the measurement volume with a non-zero velocity. In other words, the power of the frequency-shifted portion 1004 will be proportional to the number of scattering particles, namely blood cells, in the measurement volume assuming. The non-shifted portion 1002 corresponds to the power of received light due to total backscattering by both moving blood cells and non-moving or slowly moving particles including, for example, arterial walls and other biological tissue.

The velocity v of blood may be determined from the characteristic Doppler shift $\Delta f$ in the backscattered light. The arterial lumen (or blood volume) V may be determined from the intensity of the backscattered light, for example, from the root mean square of the frequency-shifted portion 1004 of the detected signal. Assuming the illuminated artery has a circular cross-section, the volume V of the illuminated artery in the region of the arterial sensor is given by $$V = \frac{\pi}{4}D_a^2 L_I$$

where $D_a$ is the diameter of the artery and $L_I$ is the length of the interference pattern. In some implementations, the volumetric blood flow Q is then determined as a product of the blood velocity v and the arterial lumen V, in some cases incorporating the effects of the velocity profile across the artery. As will described later in this disclosure, a blood pressure in the arterial can be determined based on the distension of the artery based on the arterial lumen V and blood flow Q measured at two different elevations.

In the context of ultrasonic sensing, the blood in the arteries has a different acoustic impedance than that of the surrounding or adjacent arterial walls, skin, muscle, fat, tendons, ligaments, bone, lymph or other tissues. An arterial sensor 404 configured as an ultrasonic sensor generally functions to perform measurements by transmitting ultrasonic waves at a scanning frequency to a region of interest via an ultrasonic transmitter, and by detecting a reflected signal (or signals) via one or more ultrasonic receivers. As used herein, the terms "ultrasound" and "ultrasonic wave" are used interchangeably and refer to a propagating pressure wave having a frequency greater than or equal to about 20 kilohertz (kHz), and in some implementations, in the range of about 1 Megahertz (MHz) and about 100 MHz.

Figure 11:
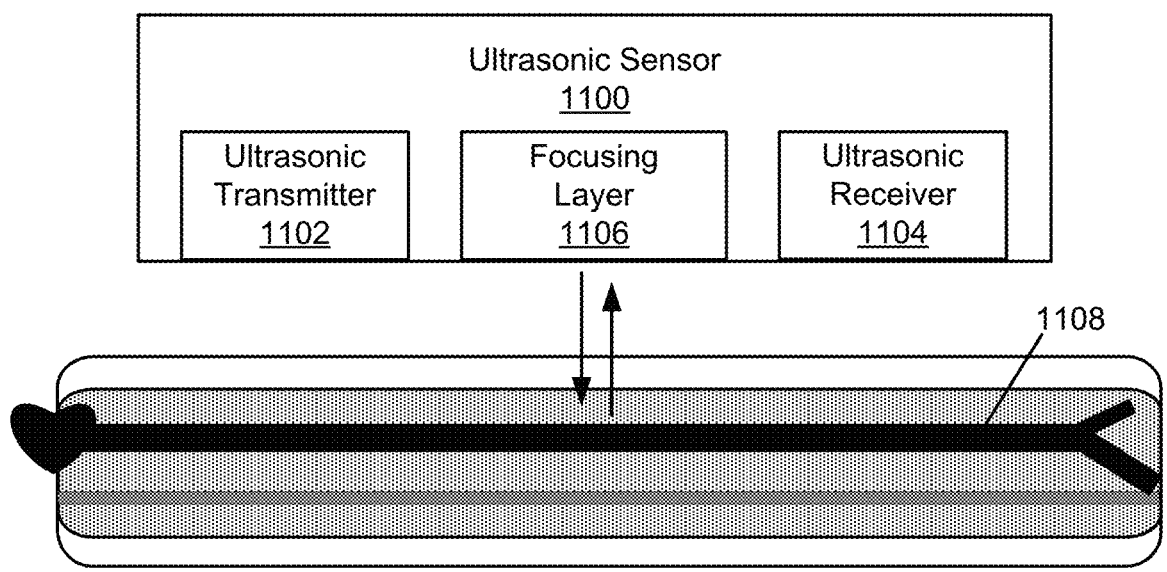
FIG. 11 shows a block diagram representation of an example ultrasonic sensor according to some implementations.

FIG. 11 shows a block diagram representation of an example ultrasonic sensor 1100 according to some implementations. For example, the ultrasonic sensor 1100 can implement one or more of the arterial sensors 404 of the blood pressure estimation device 400. The ultrasonic sensor 1100 includes an ultrasonic transducer that includes an ultrasonic transmitter 1102 and an ultrasonic receiver 1104. The ultrasonic transmitter 1102 is generally configured to generate and transmit ultrasonic waves towards a platen (a "cover plate" or "cover glass") that is in acoustical contact with the skin over the artery 1108 of interest. In some implementations, the ultrasonic transmitter 1102 may more specifically be configured to generate ultrasonic plane waves towards the platen and the artery 1108 of interest. In some implementations, the ultrasonic transmitter 1102 includes a layer of piezoelectric material such as, for example, polyvinylidene fluoride (PVDF) or a PVDF copolymer such as PVDF-TrFE. For example, the piezoelectric material of the ultrasonic transmitter 1102 may be configured to convert electrical signals provided by a controller (for example, the controller 408 described above with reference to FIG. 4) into a continuous or pulsed sequence of ultrasonic plane waves at a scanning frequency. In some implementations, the ultrasonic transmitter 1102 may additionally or alternatively include capacitive ultrasonic devices.

Figure 12:
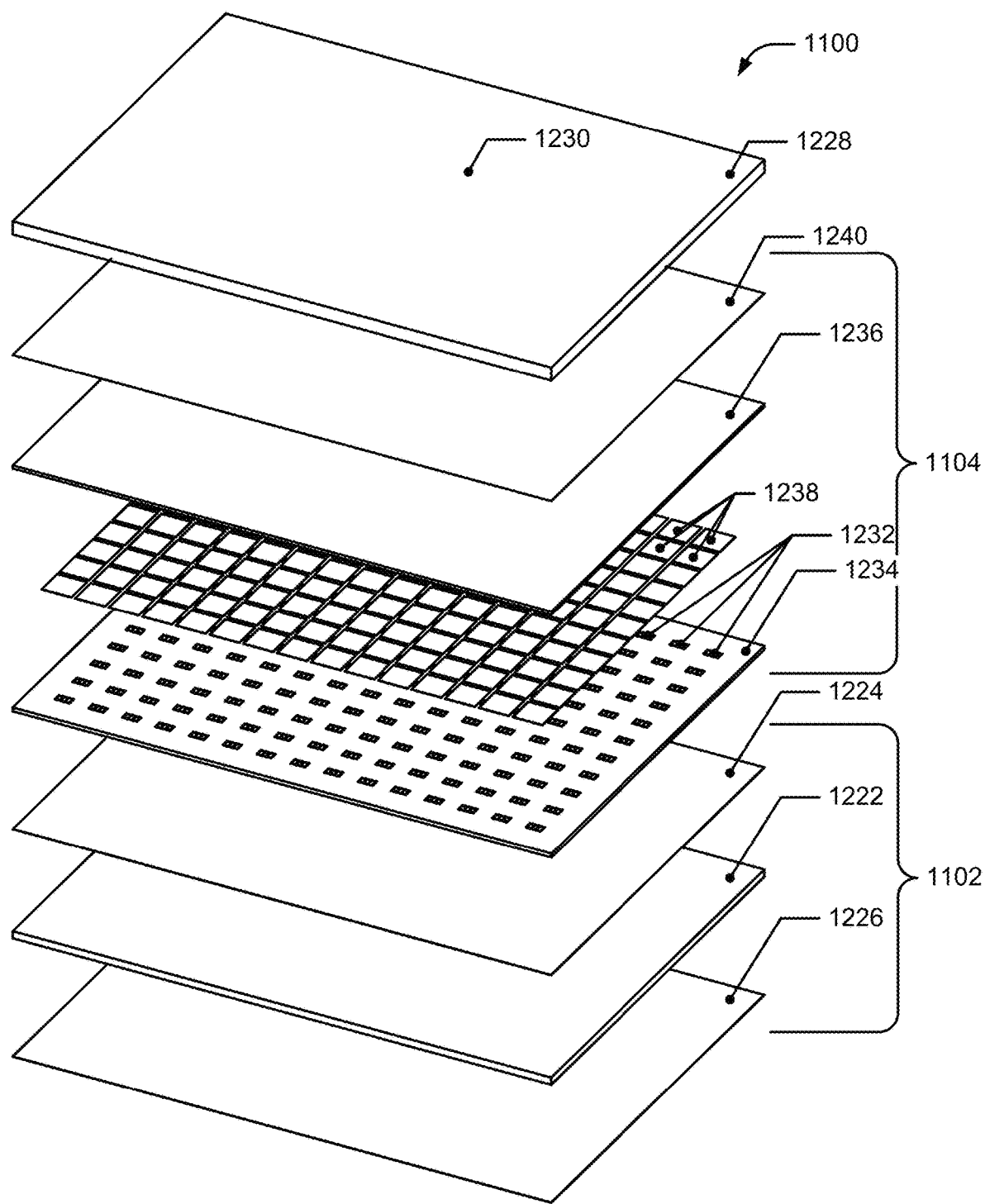
FIG. 12 shows an exploded projection view of example components of the example ultrasonic sensor of FIG. 11 according to some implementations.

The ultrasonic receiver 1104 is generally configured to detect ultrasonic reflections ("reflected waves") resulting from interactions of the ultrasonic waves transmitted by the ultrasonic transmitter 1102 with the walls of the artery of interest being scanned. The reflected waves may include scattered waves, specularly reflected waves, or both scattered waves and specularly reflected waves. In some implementations, the ultrasonic transmitter 1102 overlies the ultrasonic receiver 1104. In some other implementations, the ultrasonic receiver 1104 may overlie the ultrasonic transmitter 1102 (as shown in FIG. 12 described below). The ultrasonic receiver 1104 may be configured to generate and output electrical output signals corresponding to the detected ultrasonic reflections. In some implementations, the ultrasonic receiver 1104 may include a second piezoelectric layer different than the piezoelectric layer of the ultrasonic transmitter 1102. In some other implementations, the ultrasonic transmitter 1102 and the ultrasonic receiver 1104 may share a single piezoelectric layer. For example, the piezoelectric material of the ultrasonic receiver 1104 may be any suitable piezoelectric material such as, for example, a layer of PVDF or a PVDF copolymer. The piezoelectric layer of the ultrasonic receiver 1104 may convert vibrations caused by the ultrasonic reflections into electrical output signals. In some implementations, the ultrasonic receiver 1104 further includes a thin-film transistor (TFT) layer. In some such implementations, the TFT layer may include an array of sensor pixel circuits configured to amplify the electrical output signals generated by the piezoelectric layer of the ultrasonic receiver 1104. The amplified electrical signals provided by the array of sensor pixel circuits may then be provided as raw arterial data to a controller (for example, the controller 408 described above with reference to FIG. 4) for use in determining the blood pressure or other cardiovascular characteristics.

In some implementations, the ultrasonic sensor 1100 may further include a focusing layer 1106. For example, the focusing layer 1106 may be positioned above the ultrasonic transmitter 1102. The focusing layer 1106 may generally include one or more acoustic lenses capable of altering the paths of ultrasonic waves transmitted by the ultrasonic transmitter 1102. In some implementations, the acoustic lenses may be implemented as cylindrical lenses, spherical lenses or zone lenses. In some implementations, some or all of the lenses may be concave lenses, whereas in some other implementations some or all of the lenses may be convex lenses, or include a combination of concave and convex lenses. In some implementations, sampling strategies for processing output signals may be implemented that take advantage of ultrasonic reflections being received through a lens of the focusing layer 1106. For example, an ultrasonic wave coming back from a lens' focal point will travel into the lens and may propagate towards multiple receiver elements in a receiver array fulfilling the acoustic reciprocity principle. Depending on the signal strength coming back from the scattered field, an adjustment of the number of active receiver elements is possible. In general, the more receiver elements that are activated to receive the reflected ultrasonic waves, the higher the signal-to-noise ratio (SNR).

In some implementations that include such a focusing layer 1106, the ultrasonic sensor 1100 may additionally include one or more acoustic matching layers to ensure proper acoustic coupling between the focusing lens(es) and an object, such as a finger or wrist in contact with the platen. For example, the acoustic matching layer may include an epoxy doped with particles that change the density of the acoustic matching layer. If the density of the acoustic matching layer is changed, then the acoustic impedance will also change according to the change in density. In alternative implementations, the acoustic matching layer may include silicone rubber doped with metal or with ceramic powder. In some implementations, one or more acoustic matching layers may be positioned on one or both sides of the platen, with or without a focusing layer.

FIG. 12 shows an exploded projection view of example components of the example ultrasonic sensor 1100 of FIG. 11 according to some implementations. The ultrasonic transmitter 1102 may include a substantially planar piezoelectric transmitter layer 1222 capable of functioning as a plane wave generator. Ultrasonic waves may be generated by applying a voltage across the piezoelectric transmitter layer 1222 to expand or contract the layer, depending upon the voltage signal applied, thereby generating a plane wave. In this example, the processing unit (not shown) is capable of causing a transmitter excitation voltage to be applied across the piezoelectric transmitter layer 1222 via a first transmitter electrode 1224 and a second transmitter electrode 1226. The first and second transmitter electrodes 1224 and 1226 may be metallized electrodes, for example, metal layers that coat opposing sides of the piezoelectric transmitter layer 1222. As a result of the piezoelectric effect, the applied transmitter excitation voltage causes changes in the thickness of the piezoelectric transmitter layer 1222, and in such a manner, generates ultrasonic waves at the frequency of the transmitter excitation voltage.

The ultrasonic waves may travel towards a target region, such as an artery of interest in the finger or wrist, passing through the platen 1228. The platen 1228 may be formed of any suitable material that may be acoustically coupled to the ultrasonic transmitter 1102 or the ultrasonic receiver 1104, depending on which is adjacent the platen 1228. For example, the platen 1228 may be formed of one or more of glass, plastic, ceramic, sapphire, metal or metal alloy. In some implementations, the platen 1228 may include one or more polymers, such as one or more types of parylene, and may be substantially thinner. In some implementations, the platen 1228 may have a thickness in the range of about 10 microns (µm) to about 1000 µm or more.

A portion of the ultrasonic waves not absorbed or transmitted by the arterial walls of the artery 1108 may be reflected back through the platen 1228 and received by the ultrasonic receiver 1104. The ultrasonic receiver 1104 may include an array of sensor pixel circuits 1232 disposed on a substrate 1234 as well as a second piezoelectric receiver layer 1236. As described above, in some implementations, each sensor pixel circuit 1232 may include one or more TFT or CMOS transistor elements, electrical interconnect traces and, in some implementations, one or more additional circuit elements such as diodes, capacitors, and the like. Each sensor pixel circuit 1232 may be configured to convert an electric charge generated in the piezoelectric receiver layer 1236 proximate to the pixel circuit into an electrical signal. Each sensor pixel circuit 1232 may include a pixel input electrode 1238 that electrically couples the piezoelectric receiver layer 1236 to the sensor pixel circuit 1232.

In some implementations, the substrate 1234 may be a glass, plastic or silicon substrate upon which electronic circuitry may be fabricated. In some implementations, the substrate 1234 may be positioned between the platen 1228 and the ultrasonic transmitter 1102 or the ultrasonic receiver

1104. In some implementations, the substrate 1234 may serve as the platen 1228. One or more protective layers, acoustic matching layers, anti-smudge layers, adhesive layers, decorative layers, conductive layers or other coating layers (not shown) may be included on one or more sides of the substrate 1234 and the platen 1228.

In some implementations, a receiver bias electrode 1240 is formed or otherwise arranged on a side of the piezoelectric receiver layer 1236 proximal to the platen 1228. The receiver bias electrode 1240 may be a metallized electrode and may be grounded or biased to control which signals may be passed to the array of sensor pixel circuits 1232. Ultrasonic energy that is reflected from the exposed (upper/top) surface 1230 of the platen 1228 may be converted into localized electrical charges by the piezoelectric receiver layer 1236. These localized charges may be collected by the pixel input electrodes 1238 and passed on to the underlying sensor pixel circuits 1232. The charges may be amplified or buffered by the sensor pixel circuits 1232 and provided to the controller. The controller can be electrically connected (directly or indirectly) with the first transmitter electrode 1224 and the second transmitter electrode 1226, as well as with the receiver bias electrode 1240 and the sensor pixel circuits 1232 on the substrate 1234.

Some examples of suitable piezoelectric materials that can be used to form the piezoelectric transmitter layer 1222 or the piezoelectric receiver layer 1236 include piezoelectric polymers having appropriate acoustic properties, for example, an acoustic impedance between about 2.5 MRayls and 5 MRayls. Specific examples of piezoelectric materials that may be employed include ferroelectric polymers such as polyvinylidene fluoride (PVDF) and polyvinylidene fluoride-trifluoroethylene (PVDF-TrFE) copolymers. Examples of PVDF copolymers include 60:40 (molar percent) PVDF-TrFE, 70:30 PVDF-TrFE, 80:20 PVDF-TrFE, and 90:10 PVDR-TrFE. Other examples of piezoelectric materials that may be utilized include polyvinylidene chloride (PVDC) homopolymers and copolymers, polytetrafluoroethylene (PTFE) homopolymers and copolymers, and diisopropylammonium bromide (DIPAB).

The thickness of each of the piezoelectric transmitter layer 1222 and the piezoelectric receiver layer 1236 is selected so as to be suitable for generating and receiving ultrasonic waves, respectively. In one example, a PVDF piezoelectric transmitter layer 1222 is approximately 28 μm thick and a PVDF-TrFE receiver layer 1236 is approximately 12 μm thick. Example frequencies of the ultrasonic waves may be in the range of about 1 Megahertz (MHz) to about 100 MHz, with wavelengths on the order of a millimeter or less.

Multi-Model Blood Pressure Determination

This disclosure relates generally to devices, systems and methods for estimating various characteristics of interest (also referred to herein as "properties" or "signals") in a fluid flow system, and in particular, a pulsating fluid flow system. Various implementations are more particularly directed or applicable to devices, systems and methods for estimating various biological characteristics including, for example, dynamic or time-varying cardiovascular characteristics such as blood pressure, based at least in part on measurements of arterial data. Some implementations more specifically relate to a blood pressure estimation device for estimating a subject's transmural blood pressure based on at least two models. In some implementations, the at least two models include at least one model capable of self-calibration and at least one model capable of maintaining calibration after an initial pre-calibration. In some implementations, while capable of self-calibration, the first model can require movement or particular activity (such as a change in elevation of the blood pressure estimation device) to perform the self-calibration. In some implementations, the second model can be a non-self-calibrating blood pressure model. In some such implementations, while not capable of self-calibration, the second model can be a model that performs well at maintaining its calibration even in the absence of movement or activity (for example, while the user is sleeping).

In some implementations, during a calibration (or recalibration) operation, the self-calibrating model can be used to determine one or more calibration parameters needed for calibration based on, for example, changes in elevation associated with user movement or activity. The one or more calibration parameters can then be used in conjunction with the self-calibrating blood pressure model to determine a first value of the blood pressure. In some implementations, the first blood pressure value is then used to calibrate the second model.

In some implementations, during regular operation (after calibration), a blood pressure estimation device as disclosed herein can continuously or semi-continuously (for example, periodically) perform arterial measurements and compute a first blood pressure value based on the first self-calibrating blood pressure model, and in parallel, compute a second blood pressure value based on the second non-self-calibrating model. In some implementations, the blood pressure estimation device can then compare the first and the second blood pressure values. In some such implementations, the blood pressure estimation device can select a more reliable one of the first and the second blood pressure values to output or store. In some other implementations, the blood pressure estimation device can average or otherwise manipulate or combine the first and the second blood pressure values into a third ("final") blood pressure value to output or store. In some implementations, the blood pressure estimation device can perform a re-initialization or other re-calibration operation in which the first and the second models are re-calibrated in response to a determination that the first and the second blood pressures diverge. Such divergence can indicate that one or more of the calibration parameters have changed, for example, as a result of the arterial walls dilating or contracting or otherwise becoming more elastic (less stiff) or less elastic (more stiff).

Figure 13:
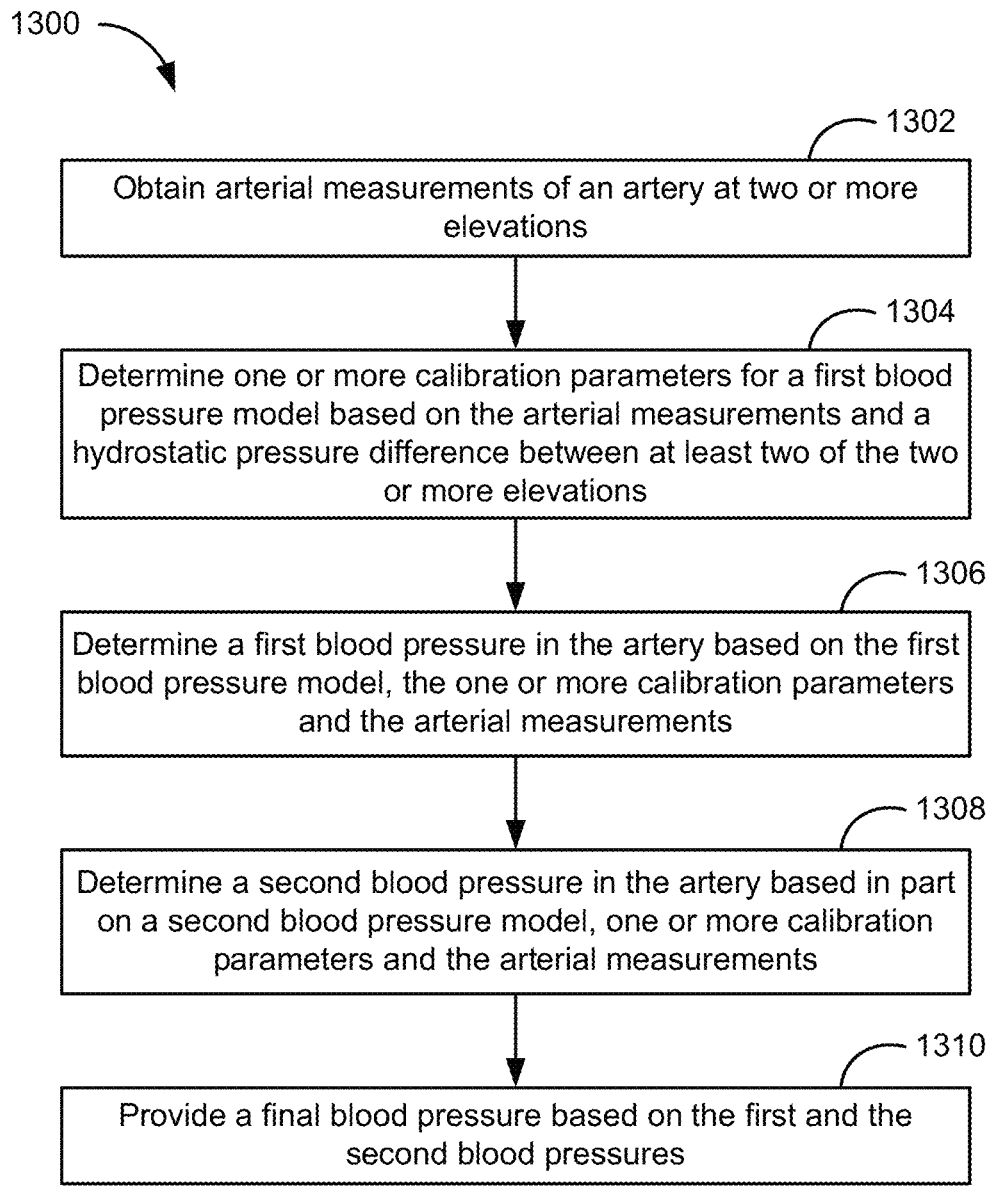
FIG. 13 shows a flow diagram of an example process for estimating blood pressure according to some implementations.

FIG. 13 shows a flow diagram of an example process 1300 for estimating blood pressure according to some implementations. For example, the process 1300 can be performed by, or responsive to instructions generated and sent by, the controller 408 of the blood pressure estimation device 400.

In some implementations, the process 1300 begins in block 1302 with obtaining arterial measurements of an artery at two or more elevations. For example, the two or more elevations can include a first elevation below a subject's heart and a second elevation approximately level with the subject's heart. In block 1304, the process proceeds with determining one or more calibration parameters for a first blood pressure model based on the arterial measurements and a hydrostatic pressure difference between at least two of the two or more elevations (for example, the first elevation and the second elevation). In some such implementations, the first blood pressure model can be a self-calibrating model. In block 1306, the process proceeds with determining a first blood pressure in the artery based on the first blood pressure model, the one or more calibration parameters and the arterial measurements. In some implementations, the process 1300 proceeds in block 1308 with determining a second blood pressure in the artery based in part on a second blood pressure model, one or more calibration parameters and the arterial measurements. In some such implementations, the second blood pressure model can be a self-calibrating model or a non-self-calibrating model. In block 1310, the process proceeds with providing a final blood pressure based on the first and the second blood pressures.

Although the process 1300 has been described as using two blood pressure models to obtain two blood pressure estimates, in some other implementations more than two (for example, three, four or more) blood pressure models can be used to determine a respective number of blood pressure estimates. For example, the process 1300 can utilize two or more self-calibrating blood pressure models and one non-self-calibrating blood pressure model; two or more non-self-calibrating blood pressure models and one self-calibrating blood pressure model; or two or more self-calibrating blood pressure models and two or more non-self-calibrating blood pressure models. The blood pressure estimates from the different blood pressure models can then be selectively combined, integrated or otherwise analyzed and used to provide the final blood pressure in block 1310.

Figure 14:
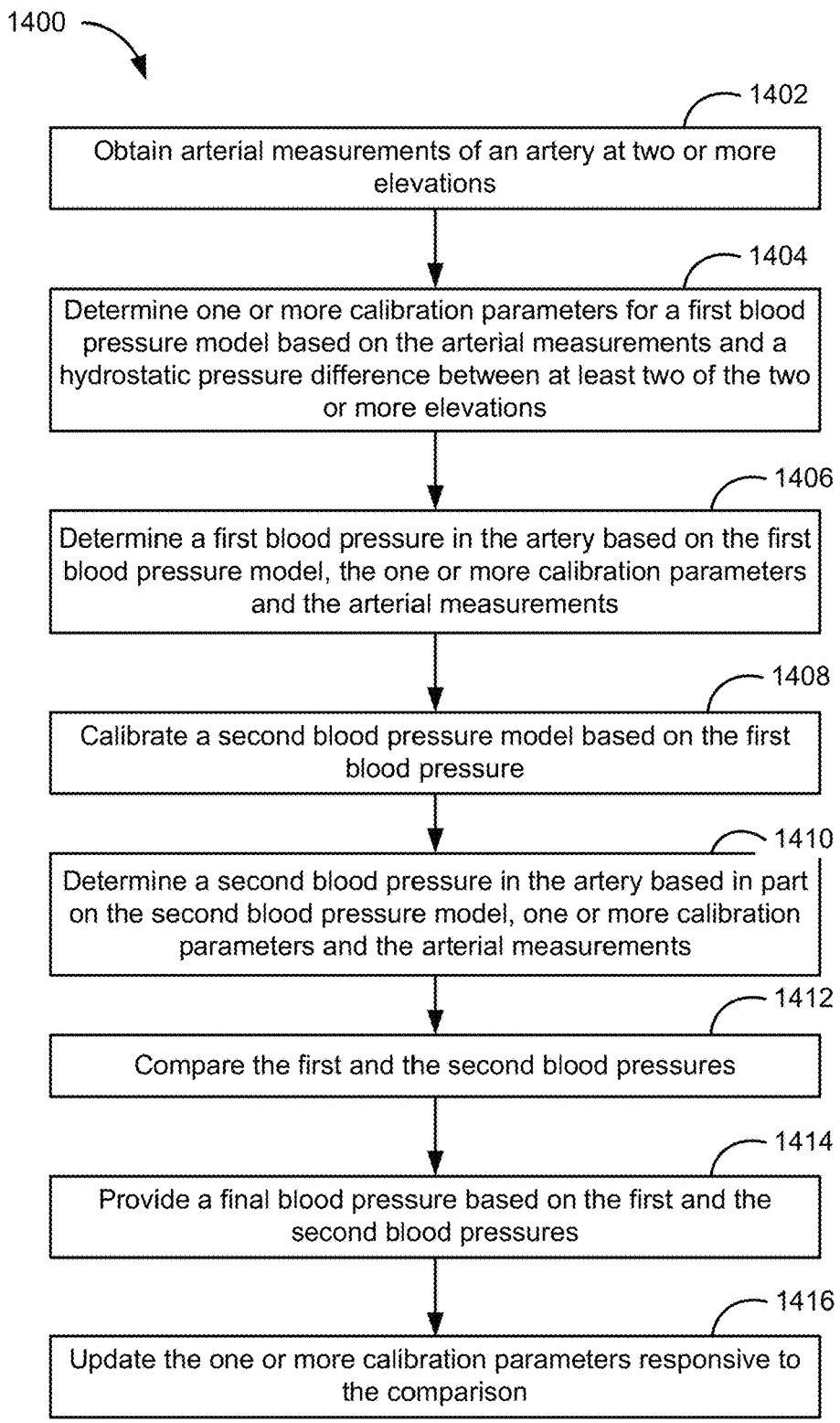
FIG. 14 shows a flow diagram of an example process for estimating blood pressure according to some implementations.

FIG. 14 shows a flow diagram of an example process 1400 for estimating blood pressure according to some implementations. For example, the process 1400 can be performed by, or responsive to instructions generated and sent by, the controller 408 of the blood pressure estimation device 400. In some implementations, the process 1400 begins in block 1402 with obtaining arterial measurements of an artery at two or more elevations. For example, the two or more elevations can include a first elevation below a subject's heart and a second elevation approximately level with the subject's heart. In block 1404, the process proceeds with determining one or more calibration parameters for a first blood pressure model based on the arterial measurements and a hydrostatic pressure difference between at least two of the two or more elevations (for example, the first elevation and the second elevation). In some such implementations, the first blood pressure model can be a self-calibrating model. In block 1406, the process proceeds with determining a first blood pressure in the artery based on the first blood pressure model, the one or more calibration parameters and the arterial measurements. In some implementations, the process 1400 proceeds in block 1408 with calibrating a second blood pressure model based on the first blood pressure. In some such implementations, the second blood pressure model can be a non-self-calibrating model. In block 1410, the process proceeds with determining a second blood pressure in the artery based in part on the second blood pressure model, one or more calibration parameters and the arterial measurements.

In some implementations, the process 1400 proceeds in block 1412 with comparing the first and the second blood pressures. For example, in some implementations, the comparison of the first and the second blood pressures additionally includes or is followed by determining whether the first and the second blood pressures diverge. For example, to determine whether the first and the second blood pressures diverge, the controller 408 can determine whether a sequence of one or more first blood pressure values (a "first blood pressure signal") estimated using the first self-calibrating blood pressure model diverge from a sequence of one or more second blood pressure values (a "second blood pressure signal") estimated using the second non-self-calibrating blood pressure model. In some implementations, to determine whether the first and the second blood pressures have diverged, a difference between the most recent first and second blood pressure values is compared with a threshold value (for example, 2 mmHg).

In some implementations, the process 1400 proceeds in block 1414 with providing a final (or "output" or "resultant") blood pressure based on the first and the second blood pressures. For example, in some implementations, if the controller 408 determines that the first and the second blood pressures do not diverge, the controller 408 selects by default a one of the first and the second blood pressure values determined using the self-calibrating or the non-self-calibrating blood pressure model, respectively, as the final blood pressure in block 1414. In some other implementations, the controller 408 can compute an average of the first and the second blood pressures and use the average as the final blood pressure in block 1414.

In some implementations, the process 1300 also proceeds to determine a final blood pressure in block 1414 even when the first and the second blood pressures do diverge. For example, in some implementations, if the controller 408 determines that the first and the second blood pressures diverge, the controller 408 selects one of the first and the second blood pressures determined to be the most reliable. For example, the controller 408 can select the one of the first and the second blood pressures having the least standard deviation as the final blood pressure in block 1414. In some other implementations, the controller 408 can select by default the one of the first and the second blood pressure values determined using the self-calibrating or the non-self-calibrating blood pressure model, respectively, as the final blood pressure in block 1414. In some other implementations, the controller 408 can select the one of the first and the second blood pressure values that is obtained using the blood pressure model that requires the most input parameters. In some other implementations, the controller 408 can select the one of the first and the second blood pressure values that is obtained using the blood pressure model that is more accurate, reliable or suitable for a given present activity state of the user. For example, the controller 408 can select the first blood pressure value if the controller 408 determines, based on the elevation data, acceleration data or other movement or position data, that the subject is active or otherwise regularly moving the blood pressure estimation device. On the other hand, the controller 408 can select the second blood pressure value if the controller 408 determines, based on the elevation, acceleration or other movement or position data, that the subject is inactive, still or otherwise not regularly moving the blood pressure estimation device. In some other implementations, the controller 408 can compute an average, weighted sum or some other linear or nonlinear combination of the first and the second blood pressures and use the combination as the final blood pressure in block 1414.

In some implementations, the providing of the final blood pressure further includes storing or communicating the final blood pressure. For example, the controller 408 can store the final blood pressure in the memory 412. Additionally or alternatively, the controller 408 can communicate the final blood pressure over one or more interfaces (such as the interface 414) to one or more internal, external or remote devices such as an integrated display, an external display, a mobile phone or other mobile computing device, or a server.

In some implementations, the process 1400 proceeds in block 1416 with updating the one or more calibration parameters responsive to the comparison of the first and the second blood pressures. For example, in some implementations, if the difference between the first and the second blood pressures is greater than the threshold value (for example, 2 mmHg), the process 1400 proceeds with updating the one or more calibration parameters in block 1416. For example, updating the one or more calibration parameters in block 1416 can include proceeding back to block 1402 whereupon a next set of arterial measurements of an artery are obtained at two or more elevations. As described above, the process 1400 may then again proceed to block 1404 whereupon the one or more calibration parameters are re-determined (or "updated," "re-calibrated" or "calibrated").

In some implementations, the determination of the one or more calibration parameters in block 1404 can be performed the first time the process 1400 is executed (for example, at each powering on, reboot, reset or other initialization or re-initialization of the device) as well as responsive to a determination, for example, in block 1416 that the first and the second blood pressures have diverged, but not otherwise performed during regular operation of the process 1400. Similarly, in some implementations, the calibration of the second non-self-calibrating blood pressure model in block 1408 can be performed the first time the process 1400 is executed (for example, at each powering on, reboot, reset or other initialization or re-initialization of the device) as well as responsive to a determination in block 1408 that the first and the second blood pressures have diverged, but not otherwise performed during regular operation of the process 1400. In some other implementations, the determination of the one or more calibration parameters in block 1404 is performed in each iteration of the process 1400. In such implementations, the one or more calibration parameters are recalibrated at each performance of the process 1400, for example, each time a blood pressure value is to be estimated or each time arterial measurements are obtained. In some implementations, the calibration of the second non-self-calibrating blood pressure model in block 1408 also is performed in each iteration of the process 1400. In some other implementations in which the one or more calibration parameters for the first self-calibrating blood pressure model are recalibrated in each iteration of the process 1400, the calibration of the second non-self-calibrating blood pressure model in block 1408 is still performed the first time the process 1400 is executed (for example, at each powering on, reboot, reset or other initialization or re-initialization of the device) as well as responsive to a determination, for example, in block 1416 that the first and the second blood pressures have diverged, but not otherwise performed during regular operation of the process 1400.

Although the process 1400 has been described as using two blood pressure models to obtain two blood pressure estimates, in some other implementations more than two (for example, three, four or more) blood pressure models can be used to determine a respective number of blood pressure estimates. For example, the process 1400 can utilize two or more self-calibrating blood pressure models and one non-self-calibrating blood pressure model; two or more non-self-calibrating blood pressure models and one self-calibrating blood pressure model; or two or more self-calibrating blood pressure models and two or more non-self-calibrating blood pressure models. The blood pressure estimates from the different blood pressure models can then be selectively combined, integrated or otherwise analyzed and used to provide the final blood pressure in block 1414.

Figure 15:
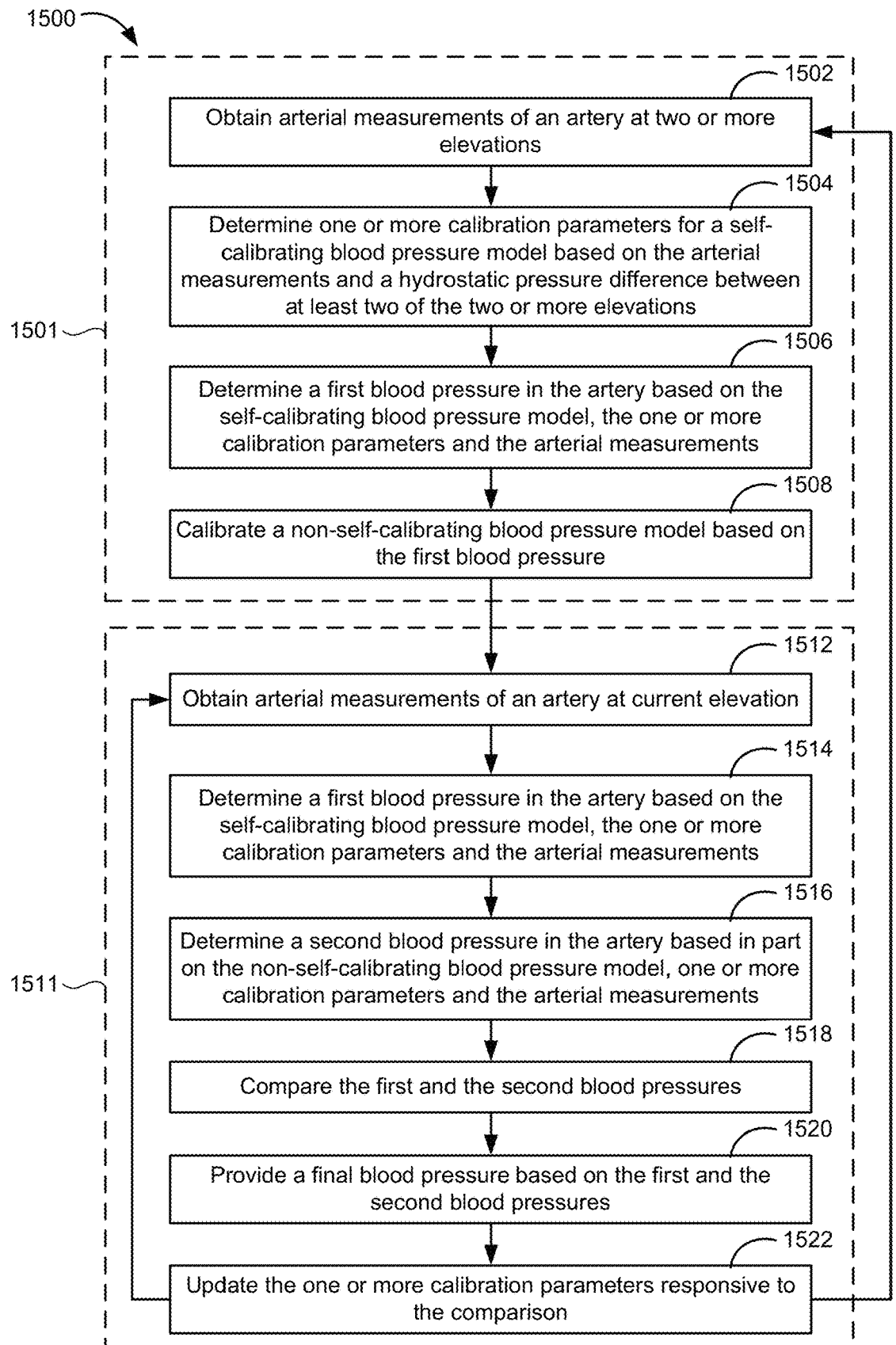
FIG. 15 shows a flow diagram of an example process for estimating blood pressure according to some implementations.

FIG. 15 shows a flow diagram of an example process 1500 for estimating blood pressure according to some implementations. For example, the process 1500 represents a more detailed example of some implementations of the blocks of the processes 1300 and 1400 described with reference to FIGS. 13 and 14, respectively. In some implementations, the process 1500 includes both an initialization (or "calibration") phase 1501 as well as a regular (or "normal") operating phase 1511. In some implementations, the initialization phase 1501 begins in block 1502 obtaining arterial measurements of an artery at two or more elevations. For example, the controller 408 can cause one or more arterial sensors 404 to perform the arterial measurements at a first elevation $h_1$ and at a second elevation $h_2$. The controller 408 also can cause the elevation sensor 406 to obtain elevation measurements at the first elevation $h_1$ and the second elevation $h_2$. For example, the first elevation $h_1$ can be an elevation below the subject's heart and the second elevation $h_2$ can be an elevation level with the subject's heart, or vice versa.

Figures 16A, 16B:
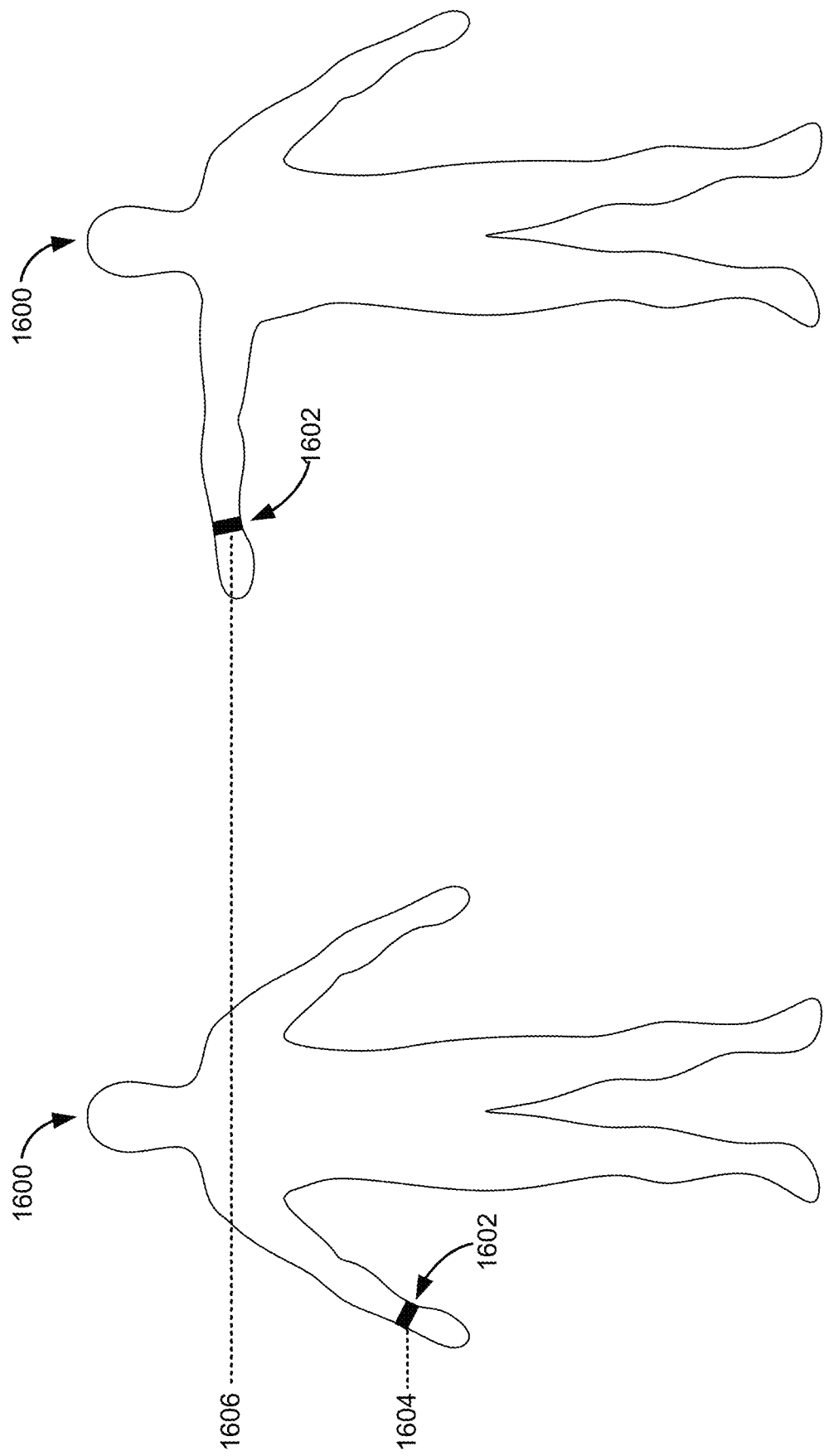
FIG. 16A shows a diagrammatic representation of a standing subject wearing a blood pressure estimation device on a wrist positioned at an elevation below the subject's heart.
FIG. 16B shows a diagrammatic representation of a standing subject wearing a blood pressure estimation device on a wrist positioned at an elevation level with the subject's heart.

FIG. 16A shows a diagrammatic representation of a standing subject 1600 wearing a blood pressure estimation device 1602 on a wrist positioned at an elevation 1604 below the subject's heart. FIG. 16B shows a diagrammatic representation of a standing subject 1600 wearing a blood pressure estimation device 1602 on a wrist positioned at an elevation 1606 level with the subject's heart. In some implementations, the blood pressure estimation device can include a display, one or more lights (for example, LEDs) or one or more sound-producing devices to alert the subject wearing the device to position and hold the device at the different elevations to enable the subsequent calibration (or recalibration) described below. While the arterial measurements at the first elevation $h_1$ and at the second elevation $h_2$ are being performed, the subject can hold the device at the first elevation or the second elevation, respectively, for at least a brief duration of time (for example, 2, 3, 4, 5, or more seconds) so that one or more cardiac cycles may elapse. It should also be appreciated that the first elevation $h_1$ and the second elevation $h_2$ can be determined as absolute elevations or as relative elevations (for example, relative to a heart level reference or relative to one another). Although the following description will be primarily described as relying on a first measurement at a first elevation below the heart and a second measurement at a second elevation level with the heart, it is not necessary that the first elevation be below the heart and the second elevation be level with the heart. For example, one or both of the first elevation and the second elevation can be above the heart. As another example, both of the first and the second elevations can be below the heart. As another example, the first elevation can be level with the heart and the second elevation can be above or below the heart.

In some implementations, the process 1500 proceeds in block 1504 with determining one or more calibration parameters for a self-calibrating blood pressure model based on the arterial measurements and a hydrostatic pressure difference between the first elevation $h_1$ and the second elevation $h_2$. In some implementations, the process then proceeds in block 1506 with determining a first blood pressure value (or simply "first blood pressure") in the artery based on the self-calibrating blood pressure model, the one or more calibration parameters and the arterial measurements. For example, the controller 408 can determine the one or more calibration parameters for the self-calibrating blood pressure model in block 1504 using the self-calibrating blood pressure model itself in conjunction with the hydrostatic pressure difference. The particular arterial sensor or sensors 404 used to obtain the arterial measurements in block 1502, as well as the particular arterial measurements performed by the arterial sensor(s) 404, will depend on the particular self-calibrating blood pressure model selected or otherwise used in blocks 1504 and 1506. Some examples of self-calibrating blood pressure models suitable for use in blocks 1504 and 1506 are described below.

Model A

Figure 17:
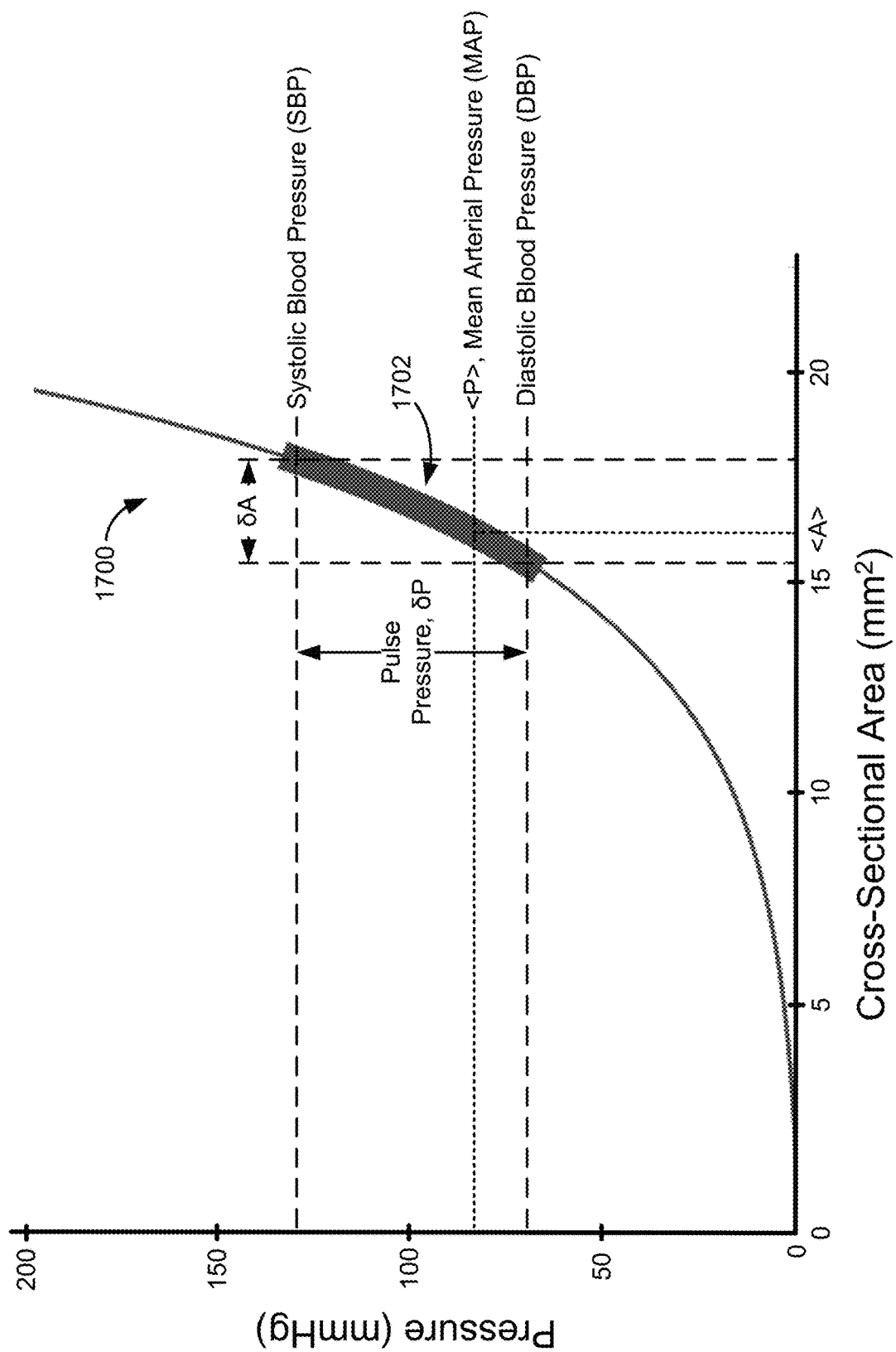
FIG. 17 shows a plot of an example blood pressure curve for an artery as a function of cross-sectional area A.

One example of a self-calibrating blood pressure model ("Model A") can be based on a stress-strain relationship such as that shown in Equation 1 below $$P = x_0 a_0 (a^A/a_0 - 1) \qquad (1),$$

where P is the transmural blood pressure, $x_0$ and $a_0$ are the calibration parameters and A is a measurement of the cross-sectional area A. FIG. 17 shows a plot of an example blood pressure curve 1700 for an artery as a function of cross-sectional area A. For example, the blood pressure curve 1700 is representative of the relationship of Equation 1. The cross-sectional area A of the artery is in units of $mm^2$ on the horizontal axis while the transmural blood pressure P is in units of mmHg on the vertical axis. A normal operating portion 1702 (denoted by a thicker portion of the exponential curve 1700) is defined at an upper end by the systolic blood pressure SBP and at a lower end by the diastolic blood pressure DBP. A difference between the systolic and diastolic pressures (the maximum and minimum pressures in a pulse respectively) reflects a pulse pressure $\delta P$. The right end of the normal operating portion 1702 represents a maximum cross-sectional area of the artery corresponding to the SBP, while the left end of the normal operating portion 1702 of the curve represents a minimum cross-sectional area of the artery corresponding to the DBP. A difference between the arterial cross-sectional areas at the SBP and DBP reflects the distension $\delta A$ of the artery that may be observed during a single cardiac cycle. A vertical dotted line in FIG. 17 represents the mean arterial cross-sectional area $\langle A \rangle$, whereas a horizontal dotted line reflects the mean arterial pressure (MAP), which is taken as the mean transmural pressure $\langle P \rangle$.

The first calibration parameter $a_0$ needed for Model A can be determined in block 1504 based on the relationship expressed in Equation 1. For example, the pulse pressure $\delta p$ may be approximated by the first derivative of Equation 1 as shown below in Equation 2:

$$\delta P = x_0 \delta A e^{\langle A \rangle}/a_0 \qquad (2),$$

where $x_0$ and $a_0$ are again the as of yet unknown parameters needed for calibration, $\langle A \rangle$ represents the mean cross-sectional area and $\delta A$ represents the arterial distension corresponding to a pulse pressure $\delta P$. Under semi-steady state (for example, slowly varying) conditions, the subject's pulse pressure $\delta P$ at two different elevations can be assumed to be constant. Thus, the ratio of Equation 2 evaluated at two different heights $h_1$ and $h_2$ may be expressed as Equation 3 below $$1 = \frac{\delta A_2}{\delta A_1} e^{(\langle A_2 \rangle - \langle A_1 \rangle)/a_0}. \qquad (3)$$

An expression for the first calibration parameter $a_0$ can thus be expressed as Equation 4 below.

$$a_0 = \frac{\langle A_2 \rangle - \langle A_1 \rangle}{\ln(\delta A_1 / \delta A_2)} \qquad (4)$$

Thus, the controller 408 can determine a value of the first calibration parameter $a_0$ in block 1504 using Equation 4 based on the associated values of the mean cross-sectional areas $\langle A_1 \rangle$ and $\langle A_2 \rangle$ and the arterial distensions $\delta A_1$ and $\delta A_2$ obtained for the first and the second elevations $h_1$ and $h_2$, respectively.

The second calibration parameter $x_0$ can be determined in block 1504 based on a hydrostatic pressure difference $\Delta P_h$ between the first and the second elevations $h_1$ and $h_2$. The hydrostatic pressure $P_h$ affects the transmural blood pressure P in a well-defined way, for example, because the circulatory system can be considered as a closed system. Generally, the hydrostatic pressure $P_h$ of any fluid can be expressed using Equation 5 below.

$$P_h = h * \rho * g \qquad (5)$$

In Equation 5, h is the height (or elevation), g is the gravitational acceleration at the elevation, and $\rho$ is the density of the fluid at the elevation. If measurements are performed at two different elevations, and assuming that there are no other appreciable changes in the cardiovascular system, then the hydrostatic pressure difference $\Delta P_h$ between the mean transmural blood pressures $\langle P_1 \rangle$ and $\langle P_2 \rangle$ at the two elevations $h_1$ and $h_2$, respectively, over a sequence of pulses is given by equation 6 below.

$$\Delta P_h = \langle P_2 \rangle - \langle P_1 \rangle = (h_2 - h_1) * \rho * g = \Delta h\, \rho g \qquad (6)$$

The density $\rho$ of whole blood is approximately 1025 $kg/m^3$. The gravitational acceleration g is approximately 9.806 $m/s^2$ at sea level (the variation of the gravitational acceleration g with latitudinal and longitudinal location on the surface of the earth is negligible).

The difference between the two mean pressures $\langle P_1 \rangle$ and $\langle P_2 \rangle$ also can be expressed by taking the difference of Equation 1 evaluated at the two pressures as shown in Equation 7 below.

$$\langle P_2 \rangle - \langle P_1 \rangle = x_0 a_0 (e^{\langle A_2 \rangle}/a_0 - e^{\langle A_1 \rangle}/a_0) \qquad (7)$$

An expression for the second calibration parameter $x_0$ can be obtained by combining equations 6 and 7 as shown in Equation 8 below.

$$x_0 = \frac{\Delta h \rho g}{a_0 \left( e^{\langle A_2 \rangle / a_0} - e^{\langle A_1 \rangle / a_0} \right)} \qquad (8)$$

Thus, the controller 408 can determine a value of the second calibration parameter $x_0$ in block 1504 using Equation 8 based on the associated values of the mean cross-sectional areas $\langle A_1 \rangle$ and $\langle A_2 \rangle$, the difference $\Delta h$ between the two elevations $h_1$ and $h_2$, and the value of the first calibration parameter $a_0$.

In some implementations, in a first aspect or sub-model of Model A, the arterial sensor 404 is configured to measure absolute values of the arterial distension $\delta A$ and the cross-sectional area A with relatively high precision, for example, ~>95% in some cases or applications. An ultrasonic sensor 1100 as described above with reference to FIGS. 11 and 12 is capable of obtaining such measurements. In some other implementations, a bioimpedance sensor, such as the bioimpedance sensor 700 described above with reference to FIG. 7, can be used to obtain the measurements. Using the absolute values of the arterial distension $\delta A$ and the cross-sectional area A, the controller 408 can determine the first blood pressure in block 1506 using the relationship expressed in Equation 1 and the now known values of the calibration parameters $a_0$ and $x_0$.

In some instances in which the output of the arterial sensor 404 exhibits a large calibration offset or bias, it can be difficult to obtain high precision measurements. Instead of relying on absolute values of the arterial distension δA and the cross-sectional area A, the controller 408 can, in a second aspect or sub-model of Model A, be additionally or alternatively configured to analyze the arterial pressure waveform to determine the blood pressure. As just described, in some implementations the arterial sensor 404 is unable or otherwise not configured to measure absolute values of the arterial distension δA and the cross-sectional area A. In some implementations, the arterial sensor 404 instead measures relative values of the arterial distension δA and the cross-sectional area A, for example, because the arterial distension signal includes a bias. The controller 408 determines the arterial pressure waveform based on the arterial distension data δA obtained for the diastolic portion of the cardiac cycle. In some such implementations, the controller 408 performs a high pass filtering operation on the arterial distension data δA, and subsequently performs an exponential fitting operation on the filtered arterial distension data. For example, the controller 408 can fit the high-pass filtered arterial distension data obtained for the diastolic phase to the exponential function expressed in Equation 9 below $$f(t,\alpha,\tau_a,\beta)=\alpha e^{-t/\tau_a}+\beta \qquad (9)$$

where α, β and $\tau_a$ are as of yet unknown parameters. In particular, the parameter $\tau_a$ is an arterial decay time constant associated with an arterial pulse. During the fitting, the controller 408 evaluates the parameters α, β and $\tau_a$ for best fit based on the arterial distension data δA.

Figure 18:
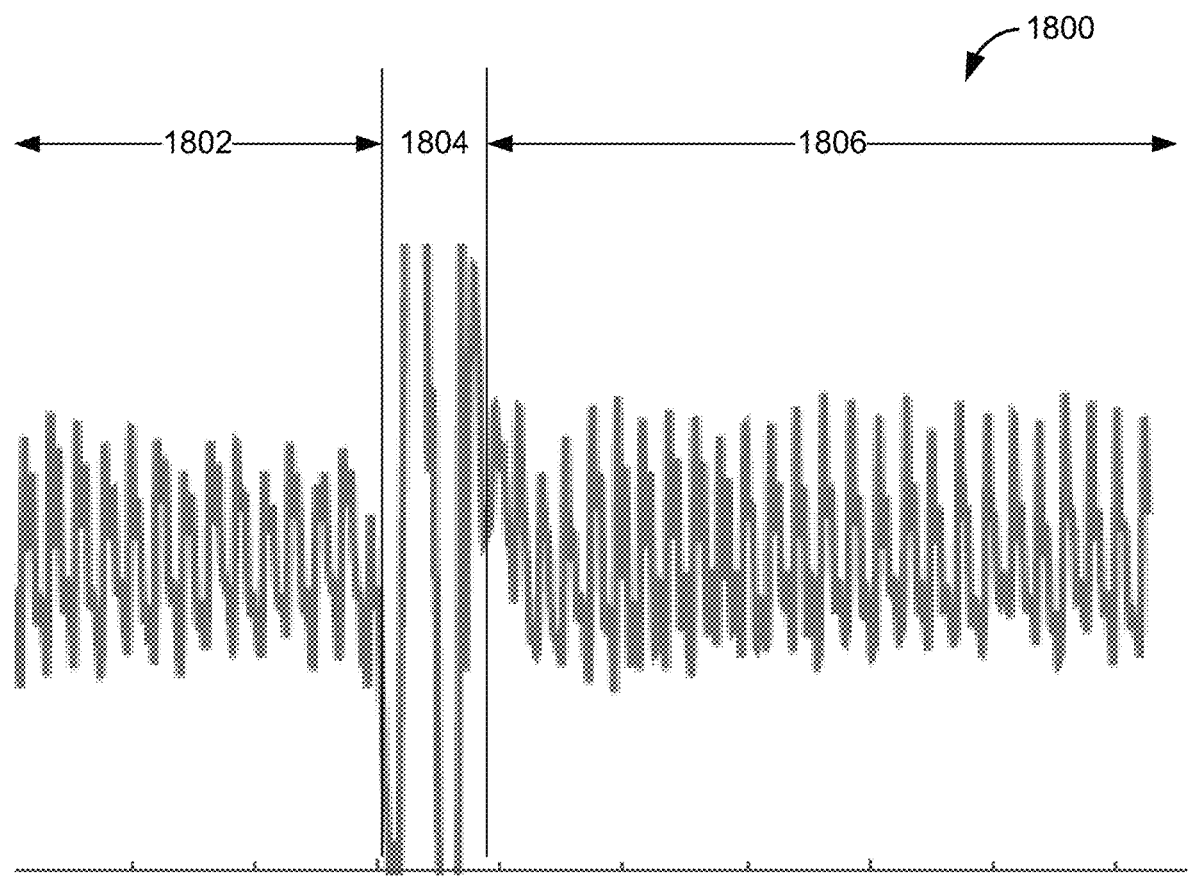
FIG. 18 shows a plot of an example arterial distension signal versus time.

FIG. 18 shows a plot of an example arterial distension signal 1800 versus time. As shown, the arterial distension signal 1800 includes a first portion or time duration 1802 during which the blood pressure estimation device is kept at a first level (for example, a heart level), a second portion 1804 during which the blood pressure estimation device is moved from the first level to a second level below the heart, and a third portion 1806 during which the blood pressure estimation device is kept at the second level. The change observed in the low frequency component of the arterial distension signal 1800 is attributed to the filling or draining of veins as a consequence of the change in the hydrostatic pressure due to the change in elevation.

The use of an ultrasonic sensor to implement the arterial sensor 404 (such as the ultrasonic sensor 1100 described above with reference to FIGS. 11 and 12) enables the controller 408 to monitor the draining and filling of the local veins in proximity to (or further away from) the artery of interest. For example, an ultrasonic arterial sensor 404 can measure the time it takes for the veins to drain and fill as the arm is moved from a first elevation $h_1$ and (for example, at the heart) to a second elevation $h_2$. (for example, below or above the heart)—a time duration referred to herein as the "venous filling time." The use of a bioimpedance sensor to implement the arterial sensor 404 (such as the bioimpedance sensor 700 described above with reference to FIG. 7) also enables the controller 408 to monitor the draining and filling of the local veins in proximity to the artery of interest. For example, a bioimpedance-based arterial sensor 404 also can measure a venous distension signal in additional to an arterial distension signal.

Figure 19:
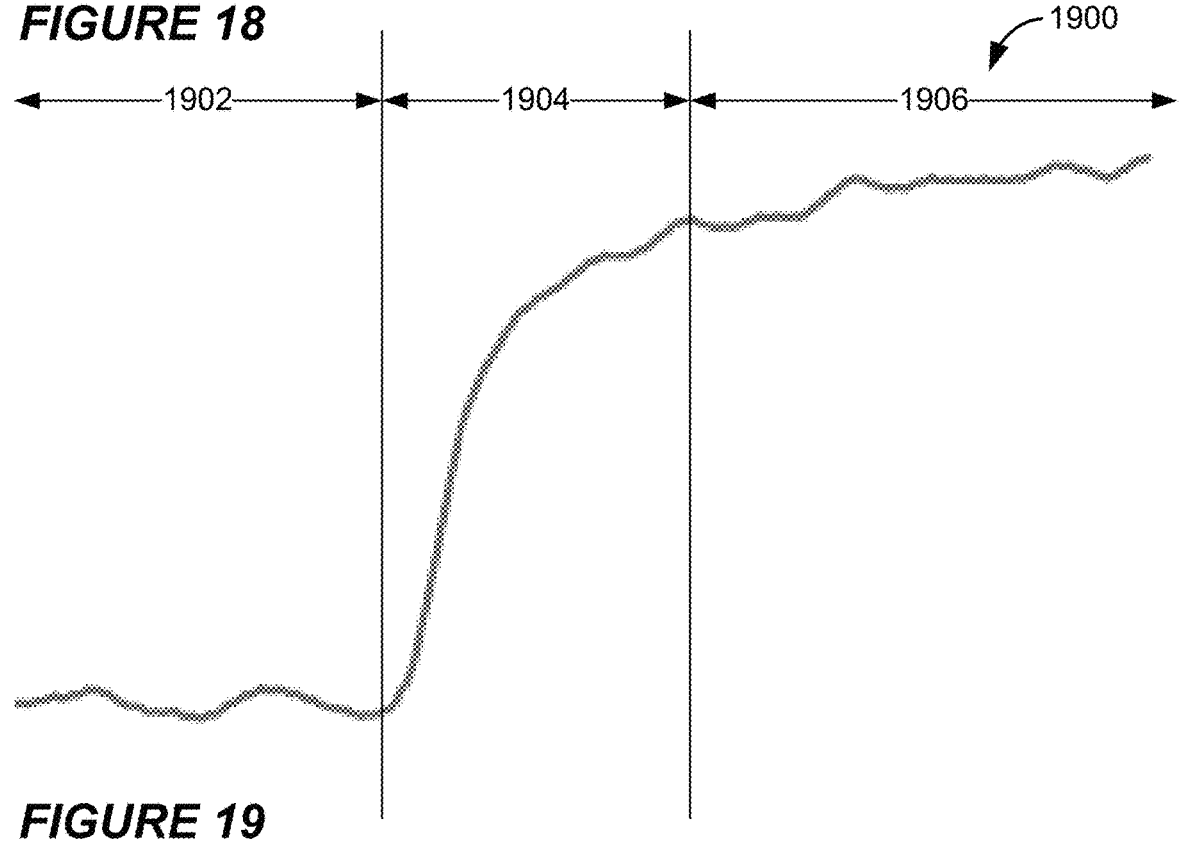
FIG. 19 shows a plot of an example venous impedance signal versus time.

FIG. 19 shows a plot of an example venous distension signal 1900 versus time. As shown, the venous distension signal 1900 also includes a first portion or time duration 1902 during which the blood pressure estimation device is kept at a first level (for example, a heart level), a second portion 1904 during which the blood pressure estimation device is moved from the first level to a second level below the heart, and a third portion 1906 during which the blood pressure estimation device is kept at the second level. The venous distension signal can be observed as a quasi-dc signal in the frequency band below that of the parallel arterial distension signal which is also recorded and which often overlaps the venous impedance signal.

In some such implementations, a low-pass filtered set of the arterial distension data also is obtained for the diastolic phase. In some implementations, the controller 408 performs a low-pass filtering operation on the arterial distension data δA, and subsequently performs an exponential fitting operation on the lowpass-filtered arterial distension data. For example, the controller 408 can fit the low-pass-filtered arterial distension data to the exponential function expressed in Equation 10 below $$f(t,\varepsilon,\tau_v)=\varepsilon e^{-t/\tau_v} \qquad (10)$$

where $\tau_v$ is an as of yet unknown venous decay time constant associated with the veins in proximity to the artery and where ε is another unknown parameter. During the fitting, the controller evaluates the parameters ε and $\tau_v$ for best fit based on the arterial distension data.

As described above with reference to FIG. 1, the ending portion of the diastolic phase 106 can generally be characterized by an exponentially decaying blood pressure that asymptotically approaches a pressure 112 referred to herein as the infinity pressure. An "infinity ratio" γ can be defined as the ratio of the arterial decay time constant to the venous decay time constant as shown in equation 11 below.

$$\gamma = \frac{\tau_a}{\tau_v} \qquad (11)$$

In some implementations, the infinity ratio is computed for each pulse. In some other implementations, the infinity ratio can be computed as an average for each of the two elevations $h_1$ and $h_2$. In some implementations, an "infinity pressure" $P_\infty$ can then be determined using equation 12 below.

$$P_\infty=(\delta A+\beta)(1+1/\gamma) \qquad (12).$$

Having the infinity pressure then enables the processor 408 to determine the offset due to the arterial sensors 404, and consequently, enables the controller 408 to determine the blood pressure in block 1506.

Model B

Another example of a self-calibrating blood pressure model ("Model B") also can be based on the stress-strain relationship expressed in Equation 1. In some implementations, the arterial measurements obtained for this self-calibrating blood pressure model include arterial distension δA measurements, arterial cross-sectional area A measurements and blood velocity v measurements. In some such implementations, the controller 408 can measure, estimate or otherwise determine arterial flow data Q based on the arterial cross-sectional area A measurements and blood velocity v measurements. In some implementations, the arterial sensor used to obtain the arterial measurements for this model can be an optical sensor such as the optical sensor 800 described above with reference to FIG. 8. In some other implementations, the arterial sensor used to obtain the arterial measurements for this model can be an ultrasonic sensor such as the ultrasonic sensor 1100 described above with reference to FIGS. 11 and 12. Because this self-calibrating blood pressure model requires measurements of the arterial blood flow Q, the arterial flow measurements can advantageously be performed by an arterial sensor especially well-suited for arterial flow measurements, such as an ultrasonic sensor or an optical sensor configured for LDV.

To illustrate this self-calibrating blood pressure model, consider that under semi-steady state (for example, slowly varying) conditions, the impedance (the fluid resistance) between the arterial system at the measurement site and the connecting venous system at the measurement site may be modelled by a resistance R. The impedance through the corresponding portion of the venous system may be modelled by a capacitance C. Because the capacitance C may be modelled as extremely large given that the venous pressure is generally close to zero, the impedance term associated with the capacitance C can be neglected. As such, analogous to Ohm's law, the transmural pressure P (analogous to a voltage in Ohm's law) may be expressed as having an electrically equivalent relationship to the blood flow Q (analogous to a current in Ohm's law), for example, as shown in equation 13 below.

$$P = R \times Q \tag{13}$$

The resistance parameter R is the unknown calibration parameter in Model B. In some implementations, the resistance parameter R may be assumed to be an unknown constant value for small variations of the transmural pressure P (for example, comparable to or smaller than the pulse pressure δP). Assuming that the resistance R is a constant value, Equation 13 may be valid for time averages of the transmural blood pressure P and the blood flow Q. For example, the mean transmural pressure ⟨P⟩ averaged over the course of one or more arterial pulses may be expressed as Equation 14 below $$\langle P \rangle = R \times \langle Q \rangle \tag{14}$$

where the mean blood flow ⟨Q⟩ may be determined in units of volume per unit time based on the measurements of the mean arterial cross-sectional area A and the blood velocity v. The difference in the mean blood pressures ⟨P₁⟩ and ⟨P₂⟩ at two elevations $h_1$ and $h_2$, respectively, can then be expressed in terms of the difference in the mean arterial flows ⟨Q₁⟩ and ⟨Q₂⟩ at the two elevations $h_1$ and $h_1$, respectively, as shown in Equation 15.

$$\langle P_2 \rangle - \langle P_1 \rangle = R(\langle Q_2 \rangle - \langle Q_1 \rangle) \tag{15}$$

Using the hydrostatic pressure relationship shown in Equation 6 in combination with Equation 15, the value of the resistance parameter R can be expressed as Equation 16 below.

$$R = \frac{(h_2 - h_1) * \rho * g}{\langle Q_2 \rangle - \langle Q_1 \rangle} \tag{16}$$

Thus, the controller can determine a value of the resistance parameter R in block 1404 using Equation 16 based on the associated values of the mean arterial flows ⟨Q₁⟩ and ⟨Q₂⟩ obtained for the first and the second elevations $h_1$ and $h_2$, respectively, as well as on the difference between the two elevations $h_1$ and $h_2$. In some other implementations, the controller actually first determines a value of the hydrostatic pressure difference $\Delta P_h$ based on Equation 6 and then determines the value of the resistance R based on Equation 15 using the result of the hydrostatic pressure difference $\Delta P_h$ from solving Equation 6. Either way, both methods for determining the value of the resistance R may in some implementations or applications be considered as involving a determination of the hydrostatic pressure difference even if a value of the hydrostatic pressure difference is not actually calculated.

In some implementations, the controller 408 estimates the calibrated mean arterial blood pressure ⟨P⟩ in block 1506 for future values of the blood flow Q using Equation 14 and the calibrated resistance parameter R from Equation 16. In some implementations, the controller 408 determines the diastolic blood pressure DBP and systolic blood pressure SDP, and thus the pulse pressure δp, using a local time dependent version of Equation 13. In some implementations, to determine the DBP and SDP, the controller 408 causes the arterial sensor 404 to obtain measurements of the maximum and minimum blood velocity amplitudes, and thus the maximum and minimum blood flow amplitudes, and correlates the maximum and minimum blood flow amplitudes to the DBP and SBP at the given elevation. In some other implementations, the controller 408 determines the pulse pressure op using a functional relationship such as that of Equation 1.

In some implementations, after the one or more calibration parameters are determined in block 1504, and after the first blood pressure is determined in block 1506, the process 1500 proceeds in block 1508 with calibrating a second non-self-calibrating blood pressure model based on the first blood pressure. In some implementations, block 1508 represents the last step or operation of the initialization phase 1501. In some other implementations, the process 1500 proceeds with determining a second blood pressure in the artery based in part on the non-self-calibrating blood pressure model, one or more calibration parameters and the arterial measurements. The particular arterial sensor or sensors 404 used to perform the arterial measurements in block 1502, as well as the arterial measurements performed by the arterial sensor(s) 404, also will depend on the particular non-self-calibrating blood pressure model selected or otherwise used. Some examples of non-self-calibrating blood pressure models suitable for use in the process 1500 are described below.

Model C

One example of a non-self-calibrating blood pressure model ("Model C") can be based on a relationship between blood pressure P and pulse wave velocity (PWV). In some implementations, the PWV can be related to the transmural blood pressure P by the Bramwell-Hill equation shown below as Equation 17.

$$PWV = \sqrt{\frac{\partial P}{\partial V} \frac{V}{\rho}} \tag{17}$$

In Equation 17, V represents the arterial lumen (blood volume) and ρ represents the blood density. The volume V can be substituted with the cross-sectional area A because the expansion of the artery in the direction of the blood flow with increasing pressure P can be neglected. This leads to the following approximation shown as Equation 18.

$$PWV \cong \sqrt{\frac{\partial P}{\partial A} \frac{A}{\rho}} \tag{18}$$

Additionally, the derivative of the pressure P with respect to area A can be approximated by the ratio of the pulse pressure δP over the distension δA of the artery. This leads to the following approximation shown as Equation 19.

$$PWV \cong \sqrt{\frac{\delta P}{\delta A}\frac{A}{\rho}} \qquad (19)$$

Equation 19 can be rewritten as Equation 20 below.

$$\frac{\partial P}{\partial A} = PWV^2 \frac{\rho}{A} \qquad (20)$$

And rewriting Equation 2 above yields Equation 21 below.

$$\frac{\delta P}{\delta A} = x_0 e^{A/a_0} \qquad (21)$$

In some implementations utilizing Model C, the blood pressure estimation device includes at least two arterial sensors 404. In some implementations, the controller 408 causes the arterial sensors 404 to obtain measurements of the time-dependent arterial cross sectional area A(t) and in parallel, to obtain measurements of the time-dependent arterial distension data. The pulse wave velocity PWV is related to the pulse transit time PTT by the separation distance between measurement locations (the distance between the active sensor areas of the arterial sensors 404). For example, the controller 408 can determine the PTT of a propagating pulse by performing arterial distension measurements associated with a pulse as the pulse propagates from a first physical location along the artery to another more distal second physical location along the artery. As described above with reference to the multi-sensor blood pressure estimation device 600 of FIGS. 6A and 6B, the arterial sensors 404 can include a first arterial sensor 604A positioned proximate a first physical location to determine a starting time (also referred to herein as a "first temporal location") at which point the pulse arrives at or propagates through the first physical location. A second arterial sensor 604B can be positioned proximate a second physical location to determine an ending time (also referred to herein as a "second temporal location") at which point the pulse arrives at or propagates through the second physical location and continues through the remainder of the arterial branch. The controller 408 determines the PTT as the temporal distance (or time difference) between the first and the second temporal locations (the starting and the ending times). Because the physical distance ΔD between the first and the second arterial sensors is known, the PWV can be estimated as the quotient of the physical spatial distance ΔD traveled by the pulse divided by the temporal distance (the PTT) the pulse takes in traversing the physical spatial distance ΔD. As such, the controller 408 can calculate the PWV as the quotient of the spatial distance ΔD divided by the PTT.

The controller 408 is capable of identifying, registering or otherwise determining the arrival or presence of a pulse at the position of the artery proximate each arterial sensor based on the arterial distension measurements received from the respective arterial sensor. In some implementations, the controller 408 is configured to register a pulse based on a detected onset of the pulse as determined from the arterial distension data. In other words, for example, when the arterial distension data obtained from the first arterial sensor indicates an onset of a pulse, the controller registers the associated time as the first temporal location. Similarly, when the arterial distension data obtained from the second arterial sensor indicates an onset of the pulse, the controller registers the associated time as the second temporal location. In some other implementations, it can be desirable to register, as the time associated with the pulse, the time at which the arterial distension data indicates that the gradient is the steepest. For example, it is generally true that the best temporal localization of any signal (a pulse wave in the present context) is associated with the time at which the gradient is steepest. The time at which the gradient is the steepest is generally not at the onset of the pulse, but instead, typically at some time during the systolic upstroke prior to the peaking at the systolic pressure.

In some such implementations, for example, when the arterial distension data obtained from the first arterial sensor indicates that the magnitude of the gradient has reached a local maximum (that is, when the gradient is the steepest during a given cardiac cycle), the controller registers the associated time as the first temporal location. Similarly, when the arterial distension data obtained from the second arterial sensor indicates that the magnitude of the gradient has reached a local maximum, the controller registers the associated time as the second temporal location. In some other implementations, when the arterial distension data obtained from the first arterial sensor indicates that the magnitude of the gradient has crossed a threshold (for example, reached or exceeded a threshold value pre-programmed into the memory or statically or dynamically determined by the controller), the controller registers the associated time as the first temporal location. Similarly, when the arterial distension data obtained from the second arterial sensor indicates that the magnitude of the gradient has crossed (for example, reached or exceeded a threshold value), the controller registers the associated time as the second temporal location.

In some implementations, each of the arterial sensors used to obtain arterial distension measurements for this model can be a bioimpedance sensor such as the bioimpedance sensor 700 described above with reference to FIG. 7. In some other implementations, each of the arterial sensors used to obtain arterial distension measurements for this model can be an optical sensor such as the optical sensor 800 described above with reference to FIG. 8. In some other implementations, each of the arterial sensors used to obtain arterial distension measurements for this model can be an ultrasonic sensor such as the ultrasonic sensor 1100 described above with reference to FIGS. 11 and 12. As described above, in some implementations, the first and the second arterial sensors are identical sensors. In such implementations, each of the first and the second arterial sensors utilizes the same sensor technology with the same sensitivity to the arterial distension signal caused by the propagating pulses, and has the same time delays and sampling characteristics.

In some implementations utilizing Model C, to calibrate the second blood pressure model based on the first blood pressure in block 1508, the controller 408 is configured to substitute the first blood pressure into Equation 1 and solve the set of Equations 1, 20 and 21 for values of the calibration parameters $a_0$ and $x_0$ to be used in Model C. In some such implementations, to determine the second blood pressure based on the non-self-calibrating blood pressure model, the controller 408 is configured to solve the set of Equations 1, 20 and 21 for the blood pressure using the values of the calibration parameters $a_0$ and $x_0$ determined in block 1508 and based on the measurements of the time-dependent arterial cross-sectional area A(t) and the PWV.

Model D

Another example of a non-self-calibrating blood pressure model ("Model D") also can be based on the set of Equations 1, 20 and 21. However, unlike in Model C, the controller 408 does not estimate the PWV based on detecting pulse transit times. Rather, the controller 408 can estimate the PWV used in the non-self-calibrating blood pressure model described as Model D based on a relationship between the arterial blood flow Q and the arterial cross-sectional area A. The arterial measurements used for this non-self-calibrating blood pressure model include arterial cross-sectional area A measurements and blood velocity v measurements. The controller 408 can measure, estimate or otherwise determine arterial flow data Q based on the arterial cross-sectional area A measurements and blood velocity v measurements. In particular, some such implementations are based on time-resolved joint measurements of the blood flow Q and arterial cross-sectional area A over the course of a sequence of pulses. In some implementations, to determine the PWV, the controller 408 can determine a derivative of the arterial flow Q with respect to the cross-sectional area A. For example, the PWV can be related to the derivative of the blood flow Q with respect to the cross-sectional area A of the artery as shown below in Equation 22.

$$PWV = \frac{dQ}{dA} \quad (22)$$

Figure 20:
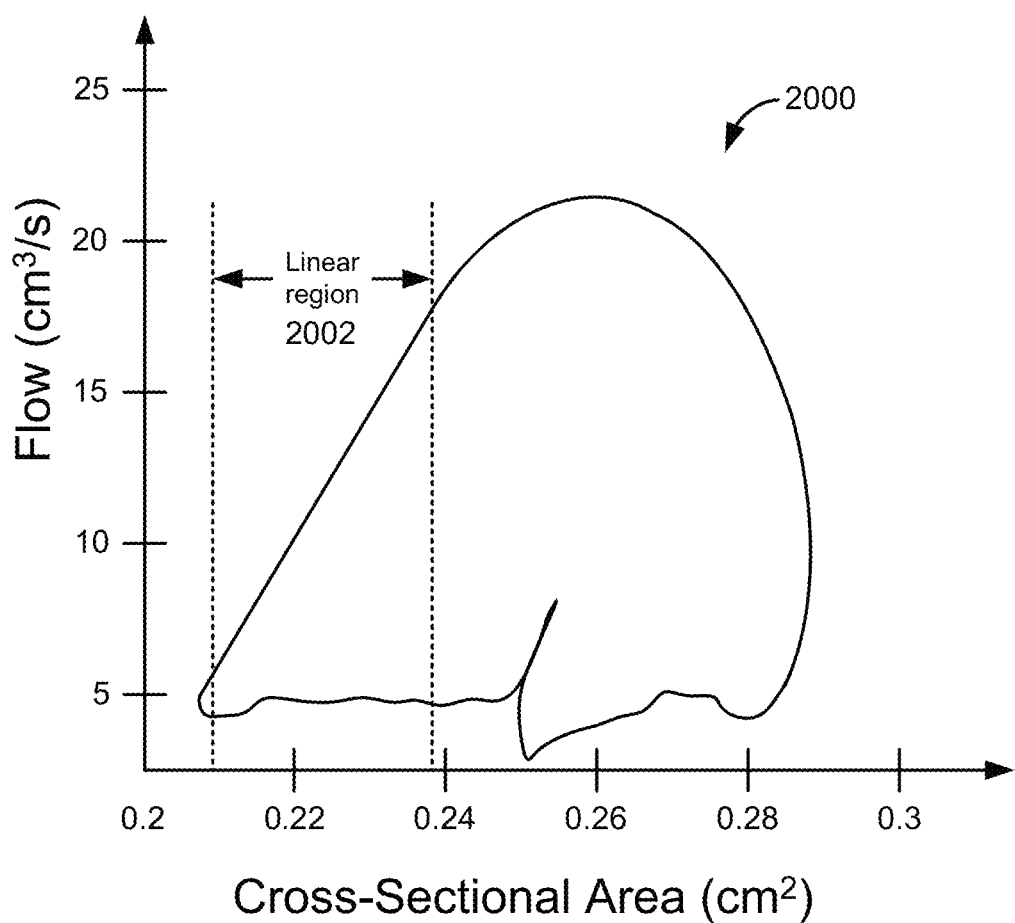
FIG. 20 shows a plot of typical changes in blood flow Q in an example artery versus cross-sectional area A during a cardiac cycle.

An approximately linear relation between the blood flow Q and the cross-sectional area A of the artery exists during the systolic phase of the cardiac cycle, and the slope of this linear relation provides for an estimate of the PWV. FIG. 20 shows a plot 2000 of typical changes in blood flow Q in an example artery versus cross-sectional area A during a cardiac cycle. The controller 408 can estimate the PWV from the linear region 2002 of the plot 2000. For example, the controller can identify the linear region 2002 by fitting the data obtained during the systolic upstroke to a linear regression and determining a derivative of the linear regression. The linear region 2002 is characterized by a portion of the data whose derivative is approximately constant. The value of the derivative (the slope of the linear regression) represents the PWV so long as the measurements are performed in or transformed into absolute units.

Because this non-self-calibrating blood pressure model (Model D) requires arterial flow measurements, the arterial sensor 404 used in conjunction with Model D can be especially well-suited to perform arterial blood velocity (and thus also blood flow) measurements. For example, in some implementations, the arterial sensor 404 used to obtain the arterial measurements for this model can be an ultrasonic sensor such as the ultrasonic sensor 1100 described above with reference to FIGS. 11 and 12. As described above, the use of an ultrasonic sensor to implement the arterial sensor 404 enables measurements of blood velocity v, and thus blood flow Q, in absolute units. In some other implementations, the arterial sensor used to obtain the arterial measurements for this model can be an optical sensor, and especially an optical sensor configured for laser Doppler velocimetry (LDV), such as the optical sensor 800 described above with reference to FIG. 8.

In some implementations utilizing Model D, to calibrate the second blood pressure model based on the first blood pressure in block 1508, the controller 408 is configured to substitute the first blood pressure into Equation 1 and solve the set of Equations 1, 20 and 21 for values of the calibration parameters $a_0$ and $x_0$ to be used in Model D. In some such implementations, to determine the second blood pressure based on the non-self-calibrating blood pressure model, the controller 408 is configured to solve the set of Equations 1, 20 and 21 for the blood pressure using the values of the calibration parameters $a_0$ and $x_0$ determined in block 1508 and based on the measurements of the time-dependent arterial cross-sectional area A(t) and the PWV.

In some implementations, after the initialization phase 1501 is complete, the process 1500 proceeds with the regular operation phase 1511 beginning in block 1512 with obtaining arterial measurements of the artery at the current elevation. In some implementations, the regular operation phase 1511 proceeds in block 1514 with determining a first blood pressure in the artery based on the self-calibrating blood pressure model, the one or more calibration parameters and the arterial measurements obtained at the current elevation. In some implementations, the process 1500 proceeds in block 1516 with determining a second blood pressure in the artery based in part on the non-self-calibrating blood pressure model one or more calibration parameters and the arterial measurements obtained at the current elevation.

In some implementations, the regular operation phase 1511 proceeds with comparing the first and the second blood pressures in block 1518. For example, the controller 408 can determine whether the first and the second blood pressures diverge in block 1518. For example, and as described above, to determine whether the first and the second blood pressures diverge, the controller 408 can determine whether a sequence of one or more first blood pressure values (a "first blood pressure signal") estimated using the first self-calibrating blood pressure model diverge from a sequence of one or more second blood pressure values (a "second blood pressure signal") estimated using the second non-self-calibrating blood pressure model. In some implementations, to determine whether the first and the second blood pressures have diverged, a difference between the most recent first and second blood pressure values is compared with a threshold value (for example, 2 mmHg).

In some implementations, the process 1500 proceeds in block 1520 with providing a final blood pressure based on the first and the second blood pressures. For example, in some implementations, if the controller 408 determines that the first and the second blood pressures do not diverge, the controller 408 selects by default a one of the first and the second blood pressure values determined using the self-calibrating or the non-self-calibrating blood pressure model, respectively, as the final blood pressure in block 1520. In some other implementations, the controller 408 can compute an average of the first and the second blood pressures and use the average as the final blood pressure in block 1520.

In some implementations, the controller 408 also proceeds to determine a final blood pressure in block 1520 even when the first and the second blood pressures do diverge. For example, in some implementations, if the controller 408 determines that the first and the second blood pressures diverge, the controller 408 selects one of the first and the second blood pressures determined to be the most reliable. For example, the controller 408 can select the one of the first and the second blood pressures having the least standard deviation as the final blood pressure in block 1520. In some other implementations, the controller 408 can select by default the a one of the first and the second blood pressure values determined using the self-calibrating or the non-selfcalibrating blood pressure model, respectively, as the final blood pressure in block 1520. In some other implementations, the controller 408 can select the one of the first and the second blood pressure values that is obtained using the blood pressure model that requires the most input parameters. In some other implementations, the controller 408 can select the one of the first and the second blood pressure values that is obtained using the blood pressure model that is more accurate, reliable or suitable for a given present activity state of the user. For example, the controller 408 can select the first blood pressure value if the controller 408 determines, based on the elevation data, acceleration data or other movement or position data, that the subject is active or otherwise regularly moving the blood pressure estimation device. On the other hand, the controller 408 can select the second blood pressure value if the controller 408 determines, based on the elevation, acceleration or other movement or position data, that the subject is inactive, still or otherwise not regularly moving the blood pressure estimation device. In some other implementations, the controller 408 can compute an average, weighted sum or some other linear or nonlinear combination of the first and the second blood pressures and use the combination as the final blood pressure in block 1520.

In some implementations, the process 1500 proceeds in block 1522 with updating the one or more calibration parameters responsive to the comparison of the first and the second blood pressures. For example, in some implementations, if the first and the second blood pressures diverge beyond the threshold value, the process 1500 returns to block 1502 to perform additional arterial measurements at two different elevations. The one or more calibration parameters for the first blood pressure model are then re-determined (or "updated," "re-calibrated" or "calibrated") by the controller 408. In some such implementations, the controller 408 also then determines another value of the first blood pressure and re-calibrates the second blood pressure model using the new value of the first blood pressure. However, in some other implementations, such as those described above with reference to the process 1400 of FIG. 14, the updating of one or more of the calibration parameters in block 1504 can be performed during each iteration of the process 1500. In some such implementations, the controller also can re-calibrate the second blood pressure model in block 1508 during each iteration of the process 1500.

In some implementations, if the first and the second blood pressures do not diverge, a next set of arterial measurements is performed in block 1512 at the next current elevation upon which the regular operation phase 1511 repeats using the next set of measurements. In such implementations, the determination of the one or more calibration parameters in block 1504 can be performed the first time the process 1500 is executed (for example, at each powering on, reboot, reset or other initialization or re-initialization of the device) as well as responsive to a determination in block 1512 that the first and the second blood pressures have diverged but otherwise not performed during regular operation of the process 1500. Similarly, in some implementations, the calibration of the second non-self-calibrating blood pressure model in block 1508 can be performed the first time the process 1500 is executed (for example, at each powering on, reboot, reset or other initialization or re-initialization of the device) as well as responsive to a determination in block 1512 that the first and the second blood pressures have diverged, but not otherwise performed during regular operation of the process 1500.

As described above, in some other implementations, such as those described above with reference to the process 1400 of FIG. 14, the updating of one or more of the calibration parameters in block 1504 can be performed during each iteration of the process 1500. In such a manner, the one or more calibration parameters are recalibrated at each performance of the process 1500, for example, each time a blood pressure value is to be estimated. In some implementations, the calibration of the second non-self-calibrating blood pressure model in block 1508 also is performed during each iteration of the process 1500. In some such implementations, the arterial sensor may be configured to (or otherwise caused by the controller to) continuously perform arterial measurements as the subject's limb (and consequently the blood pressure device) is raised or lowered between elevations. In some implementations, the arterial sensor may be configured to (or otherwise caused by the controller to) output arterial measurements in response to the elevation sensor or the controller detecting a constant or desired elevation. In this way, arterial and elevation data are available at each iteration of the process 1500.

As described above, depending on the models used as the first (self-calibrating) model and the second (non-self-calibrating) model, different sensing modalities can be used. In other words, the blood pressure estimation device can include one or more sensors of a particular type to increase, maximize or optimize the first and the second models. Said a different way, the first and the second models used by the blood pressure device can be selected to increase, maximize or optimize the particular type or types of the sensor or sensors in the blood pressure device. For example, in one example implementation of the process 1500, the controller 408 can be configured to utilize Model A and Model C. This combination does not require arterial blood flow measurements, and as such, the blood pressure estimation device need not include (but may include) an arterial sensor capable of performing arterial blood flow measurements. However, because Model C relies on PTT measurements to estimate the PWV, the blood pressure estimation device needs to include two arterial sensors. For example, the blood pressure estimation device can include two arterial sensors of the same type, for example, two bioimpedance sensors that perform all of the arterial distension and arterial cross-sectional area measurements needed for both Model A and Model C.

In another example implementation of the process 1500, the controller 408 can be configured to utilize Model A and Model D. This combination does require arterial blood flow measurements for Model D, and as such, the blood pressure estimation device includes an arterial sensor capable of performing arterial blood flow measurements. Additionally, only one arterial sensor is needed because the PWV for Model D is estimated based on arterial flow measurements not on estimated PTTs as in Model C. For example, the blood pressure estimation device can include an ultrasonic sensor that performs all of the arterial distension, arterial cross-sectional area and arterial blood flow measurements needed for both Model A and Model D. However, it can be desirable to obtain arterial data from two or more different sensor modalities to improve the robustness of the process 1400. As such, the arterial sensor used to perform the arterial distension and cross-sectional area measurements for use with Model A can be different than the arterial sensor used to perform the arterial blood flow and cross-sectional area measurements for use with Model D. For example, a bio-impedance sensor can be used to obtain the measurements for Model A while an ultrasonic sensor can be used to obtain the measurements for Model D.

In another example implementation of the process 1500, the controller 408 can be configured to utilize Model B and Model C. This combination also requires arterial blood flow measurements for Model B, and as such, the blood pressure estimation device includes an arterial sensor capable of performing arterial blood flow measurements. For example, the blood pressure estimation device can include an ultrasonic sensor that performs all of the arterial distension, arterial cross-sectional area and arterial blood flow measurements needed for both Model B and Model C. However, again, it can be desirable to obtain arterial data from two or more different sensor modalities to improve the robustness of the process 1400. As such, the arterial sensor used to perform the arterial blood flow and cross-sectional area measurements for use with Model B can be different than the arterial sensor used to perform the arterial distension and cross-sectional area measurements for use with Model C. For example, an ultrasonic sensor can be used to obtain the measurements for Model B while a bioimpedance sensor or optical sensor can be used to obtain the measurements for Model C.

In another example implementation of the process 1500, the controller 408 can be configured to utilize Model B and Model D. This combination requires arterial blood flow measurements for both Model B and Model D, and as such, the blood pressure estimation device includes an arterial sensor capable of performing arterial blood flow measurements. Additionally, only one arterial sensor is needed. For example, the blood pressure estimation device can include an ultrasonic sensor that performs all of the arterial distension, arterial cross-sectional area and arterial blood flow measurements needed for both Model B and Model D.

Although the process 1500 has been described as using two blood pressure models to obtain two blood pressure estimates, in some other implementations more than two (for example, three, four or more) blood pressure models can be used to determine a respective number of blood pressure estimates. For example, the process 1500 can utilize two or more self-calibrating blood pressure models and one non-self-calibrating blood pressure model; two or more non-self-calibrating blood pressure models and one self-calibrating blood pressure model; or two or more self-calibrating blood pressure models and two or more non-self-calibrating blood pressure models. The blood pressure estimates from the different blood pressure models can then be selectively combined, integrated or otherwise analyzed and used to provide the final blood pressure in block 1520. Generally, the more models used, the more robust the process and the more accurate the final blood pressure can be.

CONCLUSION

Various modifications to the implementations described in this disclosure may be readily apparent to those skilled in the art, and the generic principles defined herein may be applied to other implementations without departing from the spirit or scope of this disclosure. Thus, the following claims are not intended to be limited to the implementations shown herein, but are to be accorded the widest scope consistent with this disclosure, the principles and the novel features disclosed herein.

Additionally, certain features that are described in this specification in the context of separate implementations also can be implemented in combination in a single implementation. Conversely, various features that are described in the context of a single implementation also can be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Further, the drawings may schematically depict one more example processes in the form of a flow diagram. However, other operations that are not depicted can be incorporated in the example processes that are schematically illustrated. For example, one or more additional operations can be performed before, after, simultaneously, or between any of the illustrated operations. Moreover, various ones of the described and illustrated operations can itself include and collectively refer to a number of sub-operations. For example, each of the operations described above can itself involve the execution of a process or algorithm. Furthermore, various ones of the described and illustrated operations can be combined or performed in parallel in some implementations. Similarly, the separation of various system components in the implementations described above should not be understood as requiring such separation in all implementations. As such, other implementations are within the scope of the following claims. In some cases, the actions recited in the claims can be performed in a different order and still achieve desirable results.

What is claimed is:

1. A method for a biological sensor system, the method comprising:
    obtaining, by one or more arterial sensors of the biological sensor system that are coupled with a subject, two or more arterial measurements of an artery of the subject, wherein each arterial measurement of the two or more arterial measurements comprises a respective arterial distension measurement and a respective mean arterial cross-sectional area measurement;
    obtaining, by an elevation sensor of the biological sensor system, a respective elevation measurement corresponding to each arterial measurement of the two or more arterial measurements;
    receiving, at a controller of the biological sensor system that is in communication with the one or more arterial sensors and with the elevation sensor, the two or more arterial measurements from the one or more arterial sensors and the respective elevation measurements from the elevation sensor;
    determining, at the controller, a first calibration parameter and a second calibration parameter based on the two or more arterial measurements and a hydrostatic pressure difference between two elevations associated with two of the respective elevation measurements;
    determining, at the controller, a first blood pressure in the artery based on a first blood pressure model, the first calibration parameter and the second calibration parameter, and the two or more arterial measurements;
    calibrating, at the controller, a second blood pressure model based on the first blood pressure;
    determining, at the controller, a second blood pressure in the artery based in part on the second blood pressure model, the first calibration parameter and the second calibration parameter, and the two or more arterial measurements; and communicating, from the controller via one or more interfaces of the biological sensor system, a final blood pressure based on the first blood pressure and the second blood pressure.

2. The method of claim 1, further including:
comparing, at the controller, the first blood pressure and the second blood pressure; and
updating, at the controller, the first calibration parameter and the second calibration parameter responsive to the comparison.

3. The method of claim 1, wherein the determination of the first calibration parameter and the second calibration parameter includes:
determining, at the controller, a respective mean arterial distension for each of the two elevations; and
determining, at the controller, the first calibration parameter based on the respective mean arterial cross-sectional area measurements, the respective mean arterial distensions, and an arterial stress-strain relationship.

4. The method of claim 3, wherein the determination of the first calibration parameter and the second calibration parameter further includes:
determining, at the controller, the second calibration parameter based on the hydrostatic pressure difference and the first calibration parameter.

5. The method of claim 1, wherein the determination of the first blood pressure in the artery based on the first blood pressure model includes:
determining, at the controller, the first blood pressure further based on an arterial stress-strain relationship.

6. The method of claim 1, wherein:
the two or more arterial measurements further include blood velocity measurements at each of the two elevations, and
the method further includes determining, at the controller, arterial blood flow measurements based on the respective mean arterial cross-sectional area measurements and the blood velocity measurements.

7. The method of claim 6, wherein the determination of the first calibration parameter and the second calibration parameter includes:
determining, at the controller, the first calibration parameter and the second calibration parameter based on the hydrostatic pressure difference and the arterial blood flow measurements based on a linear relationship between blood pressure and blood flow.

8. The method of claim 7, wherein the determination of the first blood pressure in the artery based on the first blood pressure model includes:
determining, at the controller, the first blood pressure based on the linear relationship and the arterial blood flow measurements.

9. The method of claim 1, wherein the determination of the second blood pressure in the artery based in part on the second blood pressure model includes:
determining, at the controller, a pulse wave velocity (PWV) based on the two or more arterial measurements.

10. The method of claim 9, wherein the determination of the PWV based on the two or more arterial measurements includes:
determining, at the controller, a pulse transit time (PTT) between two arterial locations based on the two or more arterial measurements; and determining, at the controller, the PWV based on the PTT and a distance between the two arterial locations.

11. The method of claim 9, wherein:
the two or more arterial measurements further include arterial cross-sectional area measurements and arterial blood velocity measurements,
the method further includes determining, at the controller, arterial blood flow measurements based on the arterial cross-sectional area measurements and the arterial blood velocity measurements, and
the determination of the PWV based on the two or more arterial measurements includes:
determining, at the controller, a derivative of the arterial blood flow measurements with respect to the arterial cross-sectional area measurements; and
determining, at the controller, the PWV based on the derivative.

12. A biological sensor system, comprising:
one or more arterial sensors operable to couple with a subject and to obtain arterial measurements of an artery of the subject, wherein the arterial measurements each comprise a respective arterial distension measurement and a respective mean arterial cross-sectional area measurement;
an elevation sensor operable to obtain elevation measurements corresponding to the arterial measurements of the artery of the subject;
one or more processors in communication with the one or more arterial sensors and the elevation sensor, the one or more processors configured to:
receive two or more arterial measurements from the one or more arterial sensors and a respective elevation measurement for each of the two or more arterial measurements from the elevation sensor;
determine a first calibration parameter and a second calibration parameter based on the two or more arterial measurements and a hydrostatic pressure difference between two elevations associated with two of the respective elevation measurements;
determine a first blood pressure in the artery based on a first blood pressure model, the first calibration parameter and the second calibration parameter, and the two or more arterial measurements;
calibrate a second blood pressure model based on the first blood pressure; and
determine a second blood pressure in the artery based in part on the second blood pressure model, the first calibration parameter and the second calibration parameter, and the two or more arterial measurements; and
an interface in communication with the one or more processors and configured to communicate a final blood pressure based on the first blood pressure and the second blood pressure.

13. The biological sensor system of claim 12, wherein the one or more processors are further configured to:
compare the first blood pressure and the second blood pressure; and
update the first calibration parameter and the second calibration parameter responsive to the comparison.

14. The biological sensor system of claim 12, wherein the determination of the first calibration parameter and the second calibration parameter includes:
determining a respective mean arterial distension for each of the two elevations; and
determining the first calibration parameter based on the respective mean arterial cross-sectional area measurements, the respective mean arterial distensions, and an arterial stress-strain relationship.

15. The biological sensor system of claim 14, wherein the determination of the first calibration parameter and the second calibration parameter further includes:
   determining the second calibration parameter based on the hydrostatic pressure difference and the first calibration parameter.

16. The biological sensor system of claim 12, wherein:
   the two or more arterial measurements further include blood velocity measurements at each of the two elevations, and
   the one or more processors are further configured to determine arterial blood flow measurements based on the respective mean arterial cross-sectional area measurements and the blood velocity measurements.

17. The biological sensor system of claim 16, wherein the determination of the first calibration parameter and the second calibration parameter includes:
   determining each of the first calibration parameter and the second calibration parameter based on the hydrostatic pressure difference and the arterial blood flow measurements in accordance with a linear relationship between blood pressure and blood flow.

18. The biological sensor system of claim 12, wherein the determination of the second blood pressure in the artery based in part on the second blood pressure model includes:
   determining a pulse wave velocity (PWV) based on the two or more arterial measurements.

19. The biological sensor system of claim 18, wherein the determination of the PWV based on the two or more arterial measurements includes:
   determining a pulse transit time (PTT) between two arterial locations based on the two or more arterial measurements; and
   determining the PWV based on the PTT and a distance between the two arterial locations.

20. The biological sensor system of claim 18, wherein:
   the two or more arterial measurements include arterial cross-sectional area measurements and arterial blood velocity measurements,
   the one or more processors are further configured to determine arterial blood flow measurements based on the arterial cross-sectional area measurements and the arterial blood velocity measurements, and
   the determination of the PWV based on the two or more arterial measurements includes:
   determining a derivative of the arterial blood flow measurements with respect to the arterial cross-sectional area measurements; and
   determining the PWV based on the derivative.

21. A biological sensor system, comprising:
   means for measuring two or more arterial measurements of an artery of a subject, wherein each arterial measurement of the two or more arterial measurements comprises a respective arterial distension measurement and a respective mean arterial cross-sectional area measurement;
   means for measuring a respective elevation measurement corresponding to each arterial measurement of the two or more arterial measurements;
   means for receiving, the two or more arterial measurements from the means for measuring the two or more arterial measurements of the artery of the subject and for receiving the respective elevation measurements from the means for measuring the respective elevation measurement corresponding to each arterial measurement of the two or more arterial measurements;
   means for determining a first calibration parameter and a second calibration parameter based on the received two or more arterial measurements and a hydrostatic pressure difference between two elevations associated with two of the respective received elevation measurements;
   means for determining a first blood pressure in the artery based on a first blood pressure model, the first calibration parameter and the second calibration parameter, and the two or more arterial measurements;
   means for calibrating a second blood pressure model based on the first blood pressure;
   means for determining a second blood pressure in the artery based in part on the second blood pressure model, the first calibration parameter and the second calibration parameter, and the two or more arterial measurements; and
   means for communicating, from the biological sensor system, a final blood pressure based on the first blood pressure and the second blood pressure.

22. The biological sensor system of claim 21, further including:
   means for comparing the first blood pressure and the second blood pressure; and
   means for updating the first calibration parameter and the second calibration parameter responsive to the comparison.

23. One or more tangible computer-readable media storing non-transitory instructions executable by one or more processors of a biological sensor system to cause operations to be performed by the biological sensor system, including:
   obtaining, by one or more arterial sensors of the biological sensor system that are coupled with a subject and in communication with the one or more processors, two or more arterial measurements of an artery, wherein each arterial measurement of the two or more arterial measurements comprises a respective arterial distension measurement and a respective mean arterial cross-sectional area measurement;
   obtaining, by an elevation sensor of the biological sensor system in communication with the one or more processors, a respective elevation measurement corresponding to each arterial measurement of the two or more arterial measurements;
   receiving the two or more arterial measurements from the one or more arterial sensors and the respective elevation measurements from the elevation sensor;
   determining a first calibration parameter and a second calibration parameter based on the two or more arterial measurements and a hydrostatic pressure difference between two elevations associated with two of the respective elevation measurements;
   determining a first blood pressure in the artery based on a first blood pressure model, the first calibration parameter and the second calibration parameter, and the two or more arterial measurements;
   calibrating a second blood pressure model based on the first blood pressure;
   determining a second blood pressure in the artery based in part on the second blood pressure model, the first calibration parameter and the second calibration parameter, and the two or more arterial measurements; and
   communicating, from the one or more processors via one or more interfaces of the biological sensor system, a final blood pressure based on the first blood pressure and the second blood pressure.

\* \* \* \* \*